(12) United States Patent
Hayasaki et al.

(10) Patent No.: US 7,903,264 B2
(45) Date of Patent: Mar. 8, 2011

(54) STRUCTURE INSPECTION METHOD, PATTERN FORMATION METHOD, PROCESS CONDITION DETERMINATION METHOD AND RESIST PATTERN EVALUATION APPARATUS

(75) Inventors: Kei Hayasaki, Kamakura (JP); Toru Mikami, Fujisawa (JP); Shinichi Ito, Yokohama (JP); Yuichiro Yamazaki, Toyko (JP); Toshiya Kotani, Machida (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 284 days.

(21) Appl. No.: 12/198,821

(22) Filed: Aug. 26, 2008

(65) Prior Publication Data

US 2009/0002722 A1   Jan. 1, 2009

Related U.S. Application Data

(62) Division of application No. 11/051,617, filed on Jan. 27, 2005, now Pat. No. 7,483,155.

(30) Foreign Application Priority Data

Jan. 29, 2004   (JP) ................................. 2004-021647

(51) Int. Cl.
*G01B 11/14* (2006.01)
*G01F 17/50* (2006.01)

(52) U.S. Cl. ........................... 356/625; 356/394; 716/19

(58) Field of Classification Search .......... 356/625–640, 356/237.1–237.5, 445–448, 388–394; 716/19; 438/16–18
See application file for complete search history.

(56) References Cited

U.S. PATENT DOCUMENTS

| 5,523,840 A | 6/1996 | Nishizawa et al. |
| 5,587,792 A | 12/1996 | Nishizawa et al. |
| 5,963,329 A | 10/1999 | Conrad et al. |
| 6,187,488 B1 | 2/2001 | Hayasaki et al. |

(Continued)

FOREIGN PATENT DOCUMENTS

| JP | 2001-217291 | 8/2001 |
| JP | 2002-25883 | 1/2002 |
| WO | WO 03/106916 | 12/2003 |

OTHER PUBLICATIONS

Notice of Reasons for Rejection mailed by the Japanese Patent Office on Jul. 22, 2008, for Japanese Patent Application No. 2004-021647, and English-language translation thereof.

*Primary Examiner* — Sang Nguyen
(74) *Attorney, Agent, or Firm* — Finnegan, Henderson, Farabow, Garrett & Dunner, L.L.P.

(57) ABSTRACT

Wavelength dispersion of intensity of light reflected from an evaluation object is measured. A complex refractive index of a substance forming the evaluation object and the environment are prepared. Virtual component ratios comprising a mixture ratio of the substances forming the evaluation object and the environment are prepared. Reflectance wavelength dispersions to the virtual component ratios are calculated. Similar reflectance wavelength dispersions having a small difference with the measured wavelength dispersion are extracted from the reflectance wavelength dispersions. Weighted average to the virtual component ratios used for calculating the similar reflectance wavelength dispersions are calculated to obtain a component ratio of the substance forming the evaluation object and the environment so that weighting is larger when the difference is smaller. A structure of the evaluation object is determined from the calculated component ratio.

37 Claims, 21 Drawing Sheets

U.S. PATENT DOCUMENTS

| | | |
|---|---|---|
| 6,423,977 B1 | 7/2002 | Hayasaki et al. |
| 6,686,130 B2 | 2/2004 | Hayasaki et al. |
| 6,819,426 B2 * | 11/2004 | Sezginer et al. ............ 356/401 |
| 6,825,938 B2 | 11/2004 | Mikami et al. |
| 6,900,892 B2 * | 5/2005 | Shchegrov et al. ........... 356/369 |
| 6,947,141 B2 * | 9/2005 | Bischoff et al. ............... 356/369 |
| 7,321,426 B1 * | 1/2008 | Poslavsky et al. ............ 356/369 |
| 2005/0168758 A1 | 8/2005 | Hayasaki et al. |

* cited by examiner

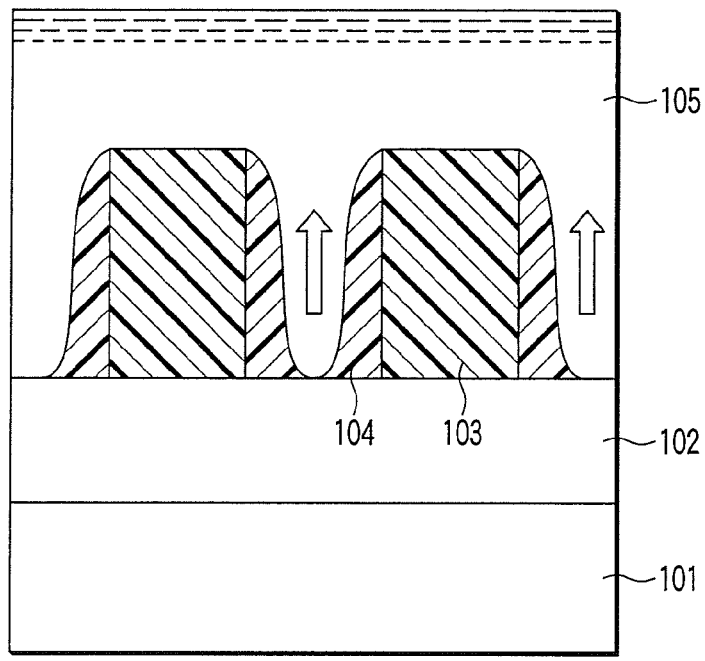
F I G. 2
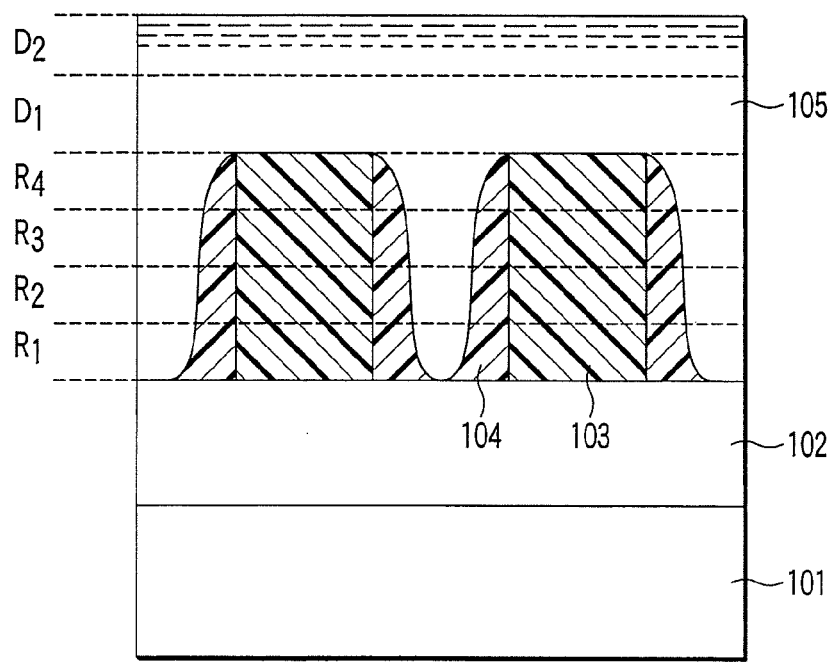
F I G. 3

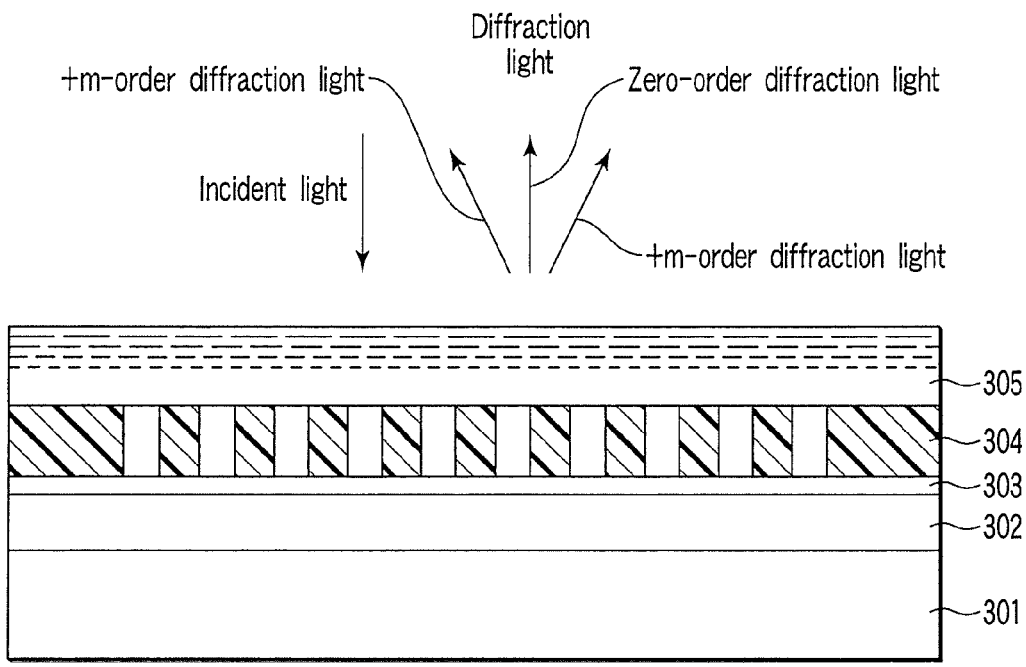
F I G. 20
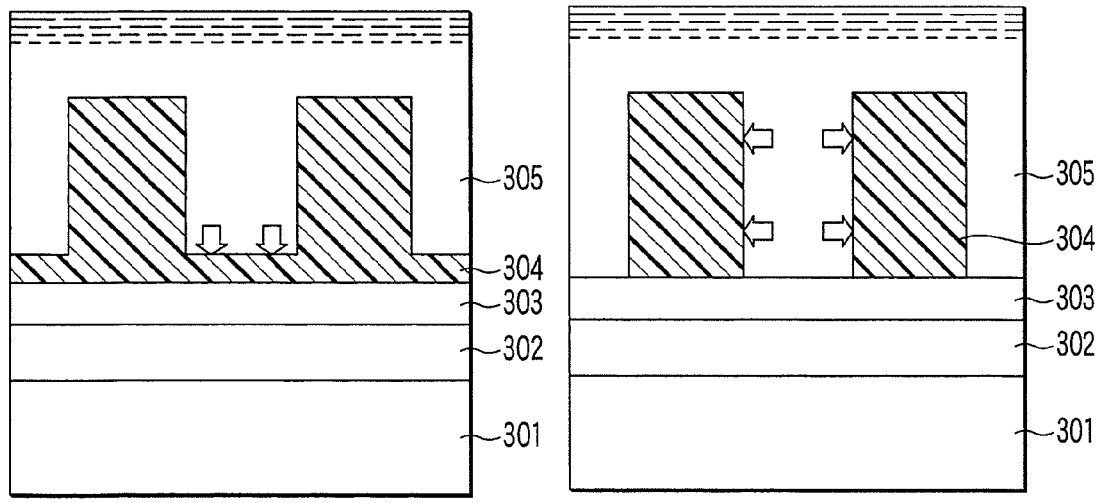
F I G. 22A  F I G. 22B

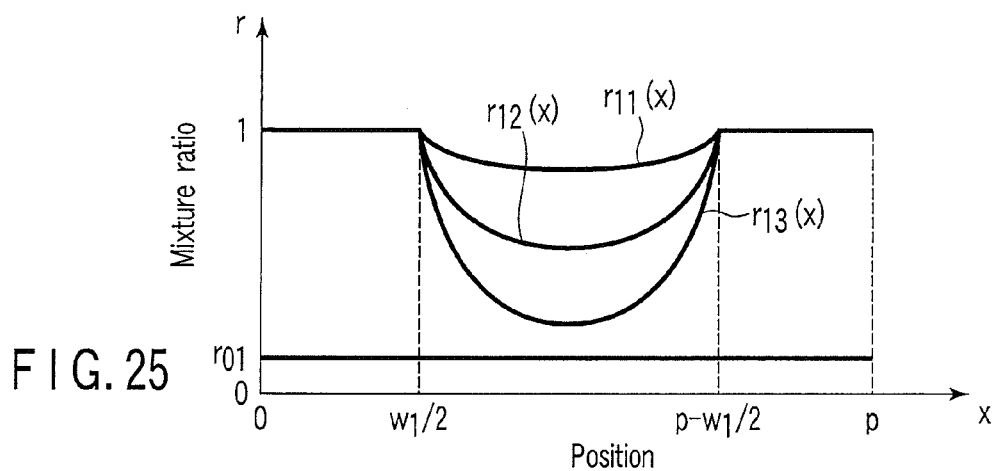
F I G. 25
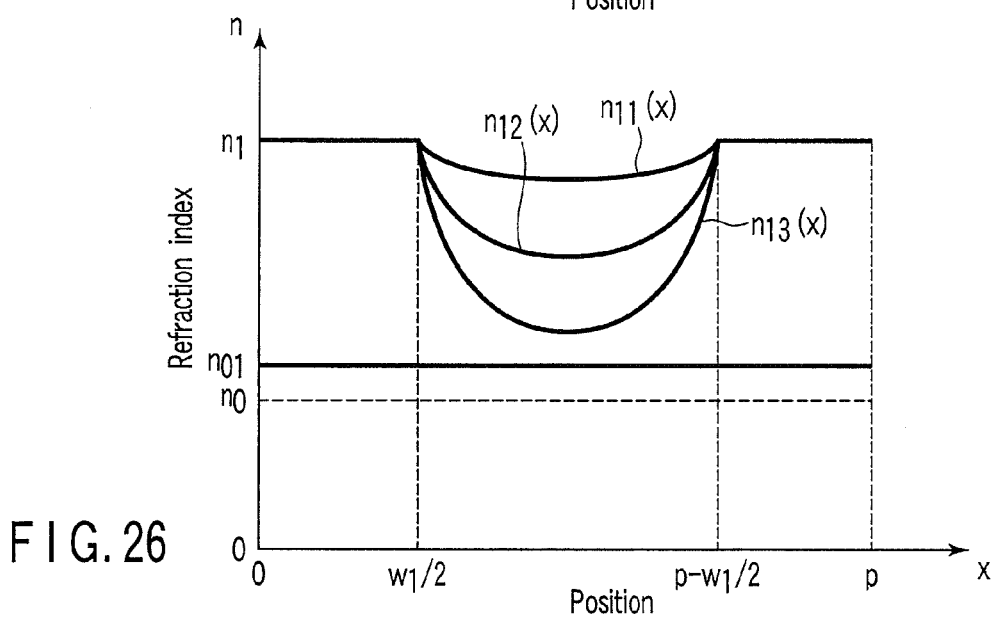
F I G. 26
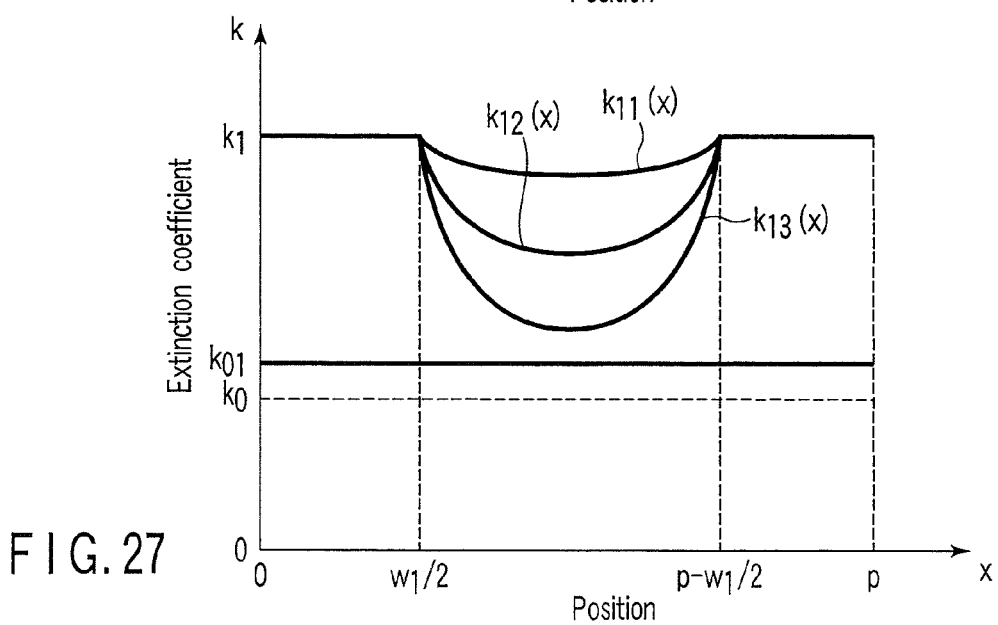
F I G. 27

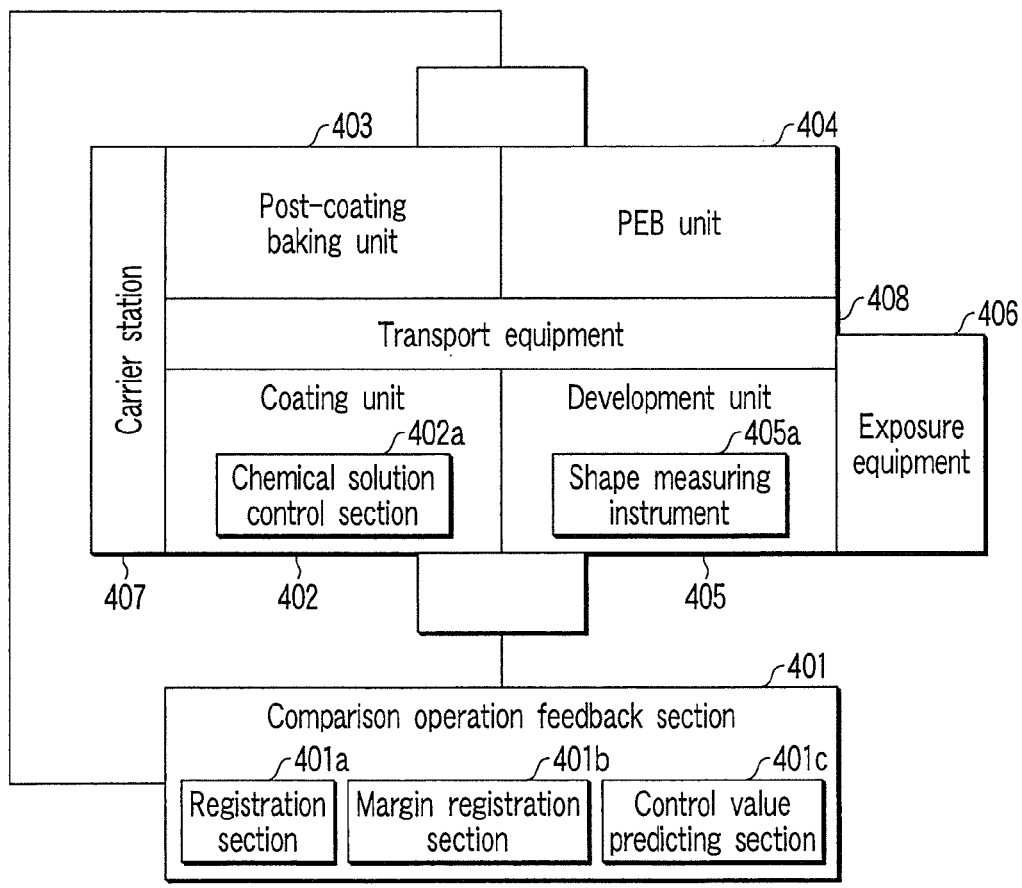
F I G. 32

STRUCTURE INSPECTION METHOD, PATTERN FORMATION METHOD, PROCESS CONDITION DETERMINATION METHOD AND RESIST PATTERN EVALUATION APPARATUS

CROSS-REFERENCE TO RELATED APPLICATIONS

This application is a division of U.S. application Ser. No. 11/051,617, filed Jan. 27, 2005 now U.S. Pat. No. 7,483,155, which is based upon and claims the benefit of priority from prior Japanese Patent Application No. 2004-021647, filed Jan. 29, 2004. The entire contents of these applications are incorporated herein by reference in their entirety.

BACKGROUND OF THE INVENTION

1. Field of the Invention

The present invention relates to a structure inspection method of inspecting the structure of an evaluation object from an intensity of reflection light of the evaluation object. Further, the present invention relates to pattern formation method, process condition determination method and resist pattern evaluation apparatus.

2. Description of the Related Art

Many reports with respect to the following method have been made. According to the method, a light incident on a pattern having a regular structure on a substrate, and the light is diffracted to obtain a diffraction light. Then, the dimension and shape of the pattern are evaluated from the measured result of the obtained diffraction light. For example, U.S. Pat. No. 5,963,329 discloses the method given below. According to the method, $\cos \Delta$ and $\tan \psi$ of a pattern having a regular structure are measured using an ellipsometer. Then, the measured values are compared with $\cos \Delta$ and $\tan \psi$ obtained from a theoretical electromagnetic wave calculation to determine the dimension. In the method, the theoretical calculation is made using the structure of a film forming a substrate and optical constant. In this case, the method is applicable to evaluation for resist pattern after development and pattern after etching. However, if the method is used for evaluating the dimension of resist pattern such that a developer film is formed on the substrate, it is impossible to accurately evaluate the pattern. This is because a mixed phase of resist reaction product and the developer exists in the vicinity of the resist pattern. According to the method disclosed in JPN. PAT. APPLN. KOKAI Publication No. 2002-25883, it is difficult to accurately evaluate the pattern. This is because a mixed phase of resist near the resist pattern and the developer is not considered like the U.S. Pat. No. 5,963,329 mentioned above.

The U.S. Pat. No. 5,963,329 further has the following disclosure. That is, theoretical wavelength dispersion of the diffraction light intensity is previously obtained by electromagnetic wave calculation using the structure of a film on the substrate and optical constant. Then, a comparison between the measured result of wavelength dispersion of the diffraction light in an actual substrate and the preceding theoretical wavelength dispersion is made to calculate the dimension and shape. This U.S. patent has disclosure of considering a composition distribution in the depth direction of the film caused by doping, and does not disclose the distribution features.

Therefore, it is impossible to accurately evaluate the pattern using the conventional method of diffracting light incident on a pattern having regular structure on a substrate, and evaluating the dimension and shape from the measured result of the obtained diffraction light.

BRIEF SUMMARY OF THE INVENTION

According to a first aspect of the present invention, there is provided a structure inspection method comprising: measuring wavelength dispersion of intensity of light reflected from an evaluation object located under an environment; preparing a complex refractive index of a substance forming the evaluation object and a complex refractive index of a substance forming the environment; setting virtual component ratios comprising a mixture ratio of the substance forming the evaluation object and the substance forming the environment in a predetermined space; making a multiple interference calculation using the complex refractive index of the substance forming the evaluation object and the complex refractive index of the substance forming the environment, thereby calculating reflectance wavelength dispersions to the virtual component ratios; extracting similar reflectance wavelength dispersions having a small difference with the measured wavelength dispersion from the reflectance wavelength dispersions; making weighted average to the virtual component ratios used for calculating the similar reflectance wavelength dispersions so that weighting is larger when the difference is smaller, thereby calculating a component ratio of the substance forming the evaluation object and the substance forming the environment; and determining a structure of the evaluation object from the calculated component ratio.

According to a second aspect of the present invention, there is provided a structure inspection method comprising: preparing a substrate having layers whose structure is characterized by an optical constant, film thickness, ratio and pitch, the substrate having one or more structure-determined layer and one or more structure-undetermined layer; preparing predicted structures of each of the layers; preparing a substrate structure library storing substrate structures comprising combinations of the structures in each of the layers; making light enter each of the substrate structures at a specified angle and calculating a light intensity of the light which is diffracted or reflected from the structure, thereby preparing a first light intensity library storing the substrate structures and the light intensity calculated to each of the substrate structures; newly preparing structures including a structure of a structure-determined layer; extracting a substrate structure including one of the newly prepared structures from the substrate structures in the first light intensity library, and preparing a second light intensity library storing the extracted substrate structure and a light intensity calculated with respect to the extracted substrate structure; making light enter the substrate at the specified angle and detecting a light intensity of light which is diffracted or reflected from the substrate; and comparing the detected light intensity with the light intensity stored in the second light intensity library to determine a structure of the substrate.

According to a third aspect of the present invention, there is provided a structure inspection method comprising: preparing a substrate having layers whose structure is characterized by an optical constant, film thickness, ratio and pitch, the substrate having one or more structure-determined layer and one or more structure-undetermined layer; preparing predicted structures of each of the layers; preparing a substrate structure library storing substrate structures comprising combinations of the structures in each of the layers; newly preparing structures of the structure-determined layers based on a structure of the structure-determined layer; extracting a substrate structure including the newly prepared structures from the first substrate structure library; preparing a second substrate structure library; predicting a light intensity of light which is diffracted or reflected from the substrate structure by calculation when making light enter each of the substrate structures in the second substrate structure library at a specified angle; making light enter the substrate at the specified angle and detecting a light intensity of light which is diffracted or reflected from the substrate; and comparing the detected light intensity with the predicted light intensity, thereby determining a structure of the substrate.

According to a fourth aspect of the present invention, there is provided a structure inspection method comprising: preparing a substrate having layers whose structure is characterized by an optical constant, film thickness, ratio and pitch, the substrate having one or more structure-determined layer and one or more structure-undetermined layer; preparing predicted structures of each of the structure-undetermined layers; preparing determined structure including a structure of the structure-determined layer; preparing a substrate structure library storing substrate structures comprising combinations of the predicted structures and the determined structure; making light enter at a specified angle the substrate structures stored in the substrate structure library and predicting a light intensity of light which is diffracted or reflected from the substrate structure by calculation; making light enter the substrate at the specified angle and detecting a light intensity of light which is diffracted or reflected from the substrate; and comparing the detected light intensity with the predicted light intensity, thereby determining a structure of the substrate.

According to a fifth aspect of the present invention, there is provided a structure inspection method of inspecting a resist pattern which is formed by development of an exposed resist film formed on a substrate, comprising: predicting an opening shape of a opening where a resist film is dissolved by developer, and predicting a distribution of a mixture ratio of a reaction product of the resist film and the developer in a liquid phase comprising the developer and the reaction product; preparing an optical constant of the resist film, the reaction product and the developer; setting structures comprising the substrate and the liquid phase based on the predicted opening shape and mixture ratio; calculating a light intensity of light which is diffracted from a substrate which has a developer film on a main surface of the substrate when making light enter the substrate at a specified angle; making light enter at the specified angle a measurement pattern on the substrate which has a developer film on a main surface of the substrate and detecting a light intensity of diffraction light from the substrate; comparing the detected intensity of the light with the calculated intensity of the light; and calculating at least one of a pattern dimension and a pattern shape of the resist film and the distribution of the ratio in the liquid phase from a best matching result in the comparison.

According to a sixth aspect of the present invention, there is provided a pattern forming method for evaluating a resist pattern which is formed by development of an exposed resist film formed on a substrate, and completing the development based on the evaluation result, comprising: predicting an opening shape of a opening where a resist film is dissolved by developer, and predicting a distribution of a mixture ratio of a reaction product of the resist film and the developer in a liquid phase comprising the developer and a reaction product of the resist film; giving a structure of a construction comprising the substrate and the liquid phase and optical constant based on a result of the prediction; predicting a light intensity of diffraction light from the construction when making light enter the construction at a specified angle; making light enter at the specified angle a measurement pattern on the substrate which has a developer film on a main surface of the substrate and detecting an intensity of diffraction light from the substrate; comparing the detected intensity of the diffraction light with the predicted intensity of the diffraction light; calculating a pattern dimension of the resist film from a best matching result in the comparison; and completing the development based on the pattern dimension.

According to a seventh aspect of the present invention, there is provided a method of determining a process condition, comprising: planning an experiment, in which experiment conditions are changed among two or more levels, the experiment conditions including a condition of controlling resist solution, a condition of forming a resist film, an exposure condition of forming a latent image on the resist film, a condition of baking a resist film formed with the latent image, and a condition of developing the resist film to form a resist pattern; changing exposure amount or defocus amount to form a latent image on the resist film, thereby forming the resist pattern based on the experiment; carrying out a measurement which includes making light enter at a specified angle a substrate which has a resist pattern thereon, detecting a light intensity of light which is diffracted or reflected from the substrate, and measuring a shape of the resist pattern using the detected light intensity and an optical constant of a material forming the substrate; calculating a process margin of exposure amount or defocus amount obtained under a level of experiment conditions based on the measured shape of the resist pattern; and predicting a combination of levels of the experiment conditions that realizes a higher process margin than a predetermined value from a relationship between levels of the experiment conditions and the process margin of the exposure amount or defocus amount.

According to a eighth aspect of the present invention, there is provided a resist pattern evaluation apparatus comprising: latent image forming section forming a latent image on a resist film on a substrate while changing exposure amount or defocus amount; bake section baking the resist film formed with the latent image; a process unit having development section developing the resist film to form a resist pattern; resist pattern measurement section measuring a shape of the resist pattern; and margin calculation section calculating a margin of exposure amount or defocus amount from a shape measurement value of the resist pattern corresponding to the exposure amount or defocus amount.

BRIEF DESCRIPTION OF THE SEVERAL VIEWS OF THE DRAWING

FIG. 2 is a cross-sectional view showing the development progress of a resist film;

FIG. 3 is a cross-sectional view showing the layer structure along the film thickness direction prepared based on a development progress model;

FIG. 20 is a schematic view showing the pattern evaluation during development;

FIG. 22A and FIG. 22B are each schematic views showing the development progress of a resist film;

FIG. 25 is a chart showing the distribution of a mixture ratio of developer and reaction product;

FIG. 26 is a chart showing the distribution of an refractive index based on a model of the third embodiment;

FIG. 27 is a chart showing the distribution of an extinction coefficient based on a model of the third embodiment;

FIG. 32 is a view showing the configuration of a photosensitive resin pattern forming system according to a fifth embodiment of the present invention.

DETAILED DESCRIPTION OF THE INVENTION

Figure 1:
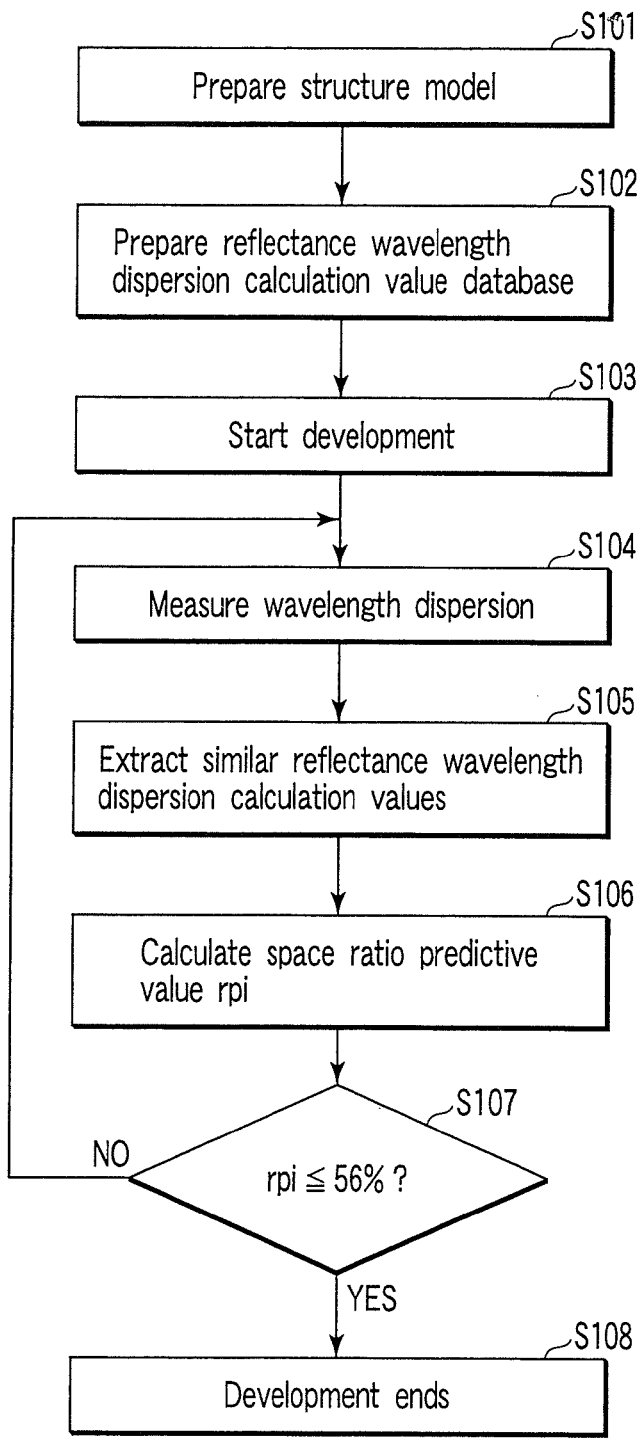
FIG. 1 is a flowchart to explain a method of determining the structure of an evaluation object according to a first embodiment of the present invention.

Embodiments of the present invention will be described below with reference to the accompanying drawings. In the following description, the same reference numerals are used to designate components having the identical function and configuration, and the overlapping explanation is given if necessary.

(1) First Embodiment

The first embodiment shows an application example to a process given below. According to the process, an anti-reflection film is formed on a Si substrate, and thereafter, ArF chemically amplified resist is further formed thereon to have a film thickness of 300 nm. A pattern for processing (etching) a front-end film is exposed onto the resist film using an ArF stepper, and thereafter, baked. Development is carried out, and thereby, the following resist pattern is formed. The resist pattern has a pitch of 260 nm and a resist remaining dimension of 115 nm (ratio of the resist pattern to pitch=0.442:0.558 in developer ratio).

FIG. 1 is a flowchart to explain a method of determining the structure of an evaluation object according to a first embodiment of the present invention.

A model used for calculating the profile of a resist film under development is prepared (step S101). The model corresponds to a typical state of developer and resist during development. A reaction product of the developer and the resist is generated from the developing resist pattern. In the following description, a developer containing a resist reaction product is called a mixed phase, and a ratio of the resist in the mixed phase is defined as a mixture ratio. In general, the diffusion velocity of the reaction product is not so fast. For this reason, if the diffusion of the reaction product, that is, a distribution of the mixture ratio in liquid phase is not taken into account in a model, the accuracy of developing pattern evaluation is worsened. In order to solve the foregoing problem, a development model considering the distribution is determined in a library preparation process in the first embodiment.

The method of forming the model will be described below. FIG. 2 is a schematic view showing the development progress. In the initial development, the development to an exposed resist film 104 advances to the film thickness direction as seen from FIG. 2. As a result, reaction products diffuse to the direction shown by an arrow. Therefore, the mixture ratio has a film thickness distribution and decreases as the position gradually gets away from the substrate. When the development in the film thickness direction ends, development advances laterally. Thus, a developer model such that a ratio of developer occupying a space increases toward the arrow direction is presumed. In FIG. 2, a reference numeral 101 denotes a silicon substrate, 102 denotes anti-reflection film, 103 denotes a non-exposed resist film, and 105 denotes a developer.

The following is a description of the step of giving substrate structure and optical constant. FIG. 3 is a cross-sectional view showing the layer structure in the film thickness direction prepared based on the above-mentioned model. Layers $D_1$ and $D_2$ comprises the developer and the mixed phase of reaction product of resist. Layers $R_1$ to $R_4$ comprises the developer, the mixed phase of reaction product of resist and resist pattern. The layers $D_1$ and $D_2$ differ from each other in a mixture ratio of the reaction product. Likewise, the layers $R_1$ to $R_4$ differ from each other in a mixture ratio of the reaction product. The reaction product is generated in the interface between the resist and the developer, and gradually diffuses to the developer layer. Therefore, the ratio of the reaction product is high at the bottom portion of the pattern.

Several virtual component ratios presuming the ratio of each substance forming evaluation object and measurement environment are set. In each layer, several ratios of each substance occupied in a space are set.

TABLE 1

| Film structure | Classification of film structure | Range of ratio | Step of ratio (%) |
|---|---|---|---|
| Developer layer | Layer $D_2$ | Developer/space = ratio of layer $D_1$-1.00 | 0.05 |
| | Layer $D_1$ | Developer/space = 0.80-1.00 | 0.05 |
| Resist layer | Layer $R_4$ | Developer/space = ratio of layer $R_3$-1.00 | 0.10 |
| | Layer $R_3$ | Developer/space = ratio of layer $R_2$-0.70 | 0.10 |
| | Layer $R_2$ | Developer/space = ratio of layer $R_1$-0.70 | 0.10 |
| | Layer $R_1$ | Developer/space = 0-0.70 | 0.10 |
| Anti-reflection film layer | Anti-reflection film layer | Anti-reflection material/space = 1.00 (fixed) | — |
| Si substrate | Si substrate | Si/space = 1.00 (fixed) | — |

Database comprising reflectance wavelength dispersion calculation value in the ratio of each layer is prepared using conditions shown in the Table 1 (step S102). The database is prepared in the following manner. First, several ratios of each substance occupying a space are prepared under the conditions shown in the Table 1, and average optical constant is determined in accordance with these ratios. Using the optical constant, a multiple interference calculation is carried out to determine a reflectance. The wavelength dispersion of the reflectance is calculated in a range from 300 to 800 nm. In general, RCWA (Rigorous coupled-wave analysis) by Morham et al. (J. Opt. Soc. Am., Vol. 12, No. 5, May 1995 1077-1086) is used as the calculation method to obtain electric filed, magnetic field and intensity of refraction light from regular pattern using Maxwell equations. Incidentally, the optical constant of the reaction product generated from the reaction resist with developer is set to the same as that of the resist. Complex refractive index comprising a refractive index n and an extinction coefficient k may be used as the optical constant.

Average (mean) complex refractive index is determined in the following manner when developer/space=0.95 in the layer $D_2$ of the developer layer. The average complex refractive index is obtained from the following equations (1) and (2) using complex refractive index of the developer (refractive index n, extinction coefficient k)=(1.33, 0) and complex refractive index of the resist (1.67, 0.06).

Average refractive index $n$=1.33×0.95+1.67× 0.05=1.347    (1)

Average extinction coefficient $k$=0×0.95+0.06× 0.05=0.003    (2)

The substrate whose resist film has been subjected to pattern exposure to resist film and post exposure bake (PEB) is cooled, and thereafter, transferred to a development apparatus. A developer is supplied onto the main surface of the substrate to form a developer film, and then, development of a resist film is started (step S103). The resist film has a device pattern region on which a device pattern is exposed and a monitor pattern region on which a monitor pattern is exposed.

A reflectance measuring means is arranged above the exposed monitor pattern for dimension measurement. Thereafter, a change of the developing pattern is watched via observation of a change of reflectance (step S104).

Figure 4:
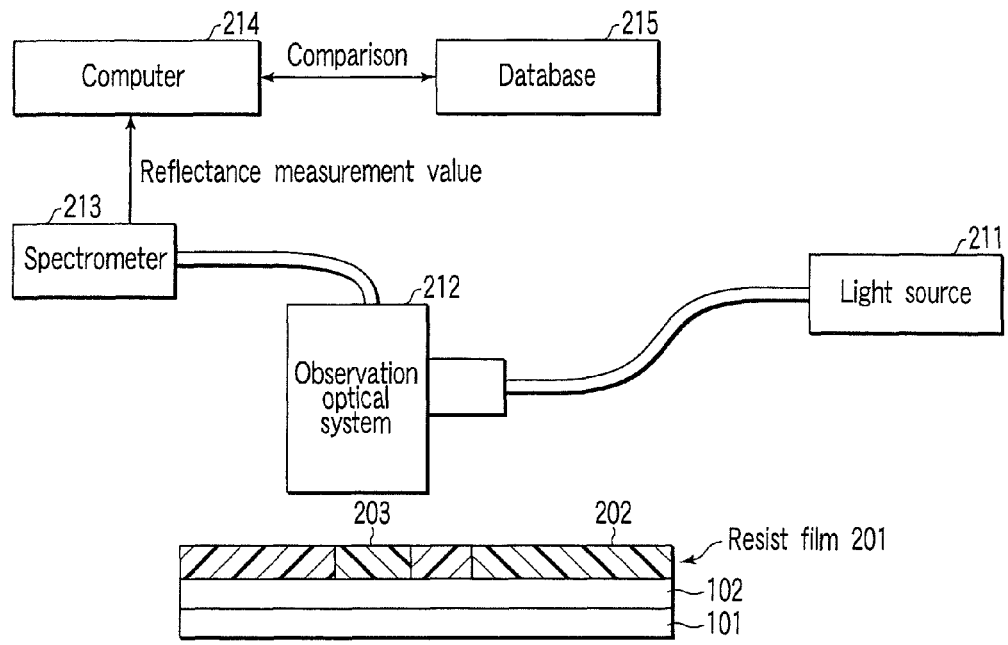
FIG. 4 is a schematic view showing the configuration of a reflectance measuring means.

FIG. 4 is a schematic view showing the configuration of the reflectance measuring means. The reflectance measuring means reflects light from a light source 211 by a mirror included in an observation optical system 212 to irradiate the light to a monitor pattern region 203 of a resist pattern 201. The monitor pattern region 203 reflects the light, and thereby, a zero-order diffraction light is generated via diffraction. The zero-order diffraction light collected to the observation optical system 212. Thereafter, the light is transmitted to a spectrometer 213 via silica optical fiber, and then, the spectrometer 213 measures wavelength dispersion of the light. A wavelength dispersion measurement value detected by the spectrometer 213 is successively sent to a computer 214. Incidentally, the monitor pattern region 203 is formed outside the device pattern region 202. A database 215 stores the reflectance wavelength dispersion calculation value calculated in step S102.

The computer 214 compares the reflectance wavelength dispersion measurement value sent from the spectrometer 213 with the wavelength dispersion calculation value stored in the database 215. Then, the computer 214 extracts some similar reflectance wavelength dispersion calculation values having the same wavelength dispersion measurement value (step S105). In this extraction, the sum of squares Si of a reflectance measurement value $r_\lambda$ at a wavelength λ and a reflectance calculation value $r_{\lambda,c}$ at the wavelength λ is calculated.

$$\text{Sum of squares} = \sum_{j=1}^{n} \frac{(r_{\lambda,j} - r_{\lambda,jc})^2}{(\lambda_n - \lambda_1)}$$

Then, the reflectance measurement value having the minimum sum of squares is retrieved in order. In the first embodiment, the reflectance calculation value less than 110% of the reflectance measurement value which makes the minimum sum of squares is retrieved.

Weighted average is taken in accordance with the sum of squares of a space ratio (component ratio), which is a base of the reflectance measurement value. By doing so, a space ratio predictive value $rp_i$ is calculated (step S106). The space ratio predictive value $rp_i$ is obtained from the following equation (4) using a space ratio $r_i$, which is a base of the reflectance measurement value, and the sum of squares Si.

$rp_i = (\Sigma r_i/s_i)/(\Sigma(1/s_i))$    (4)

Using the equation (4), each space ratio predictive value $rp_i$ of layers $R_1$ to $D_2$ is calculated. The calculated space ratio predictive value $rp_i$ is regarded as a ratio representing how much the pattern dimension occupies the pitch.

It is determined whether or not the space ratio predictive value $rp_i$ obtained based on the weighted average is equal to a predetermined value (step S107). According to the first embodiment, the predetermined value is 56%. In this embodiment, the resist pattern is formed having a pitch of 260 nm and a resist remaining dimension of 115 nm (ratio of the resist pattern to pitch=0.442:0.558 in developer ratio). Therefore, it is determined whether the space ratio predictive value $rp_i$ of the layer $R_4$ is equal to 56%.

If the space ratio predictive value $rp_i$ of the layer $R_4$ is equal to 56%, cleaning water is supplied to the substrate surface, and then, development is stopped (step S108).

If the space ratio predictive value $rp_i$ of the layer $R_4$ is not equal to 56%, development is continued, and the procedures from step S103 to S107 are repeated. When the space ratio predictive value $rp_i$ of the layer $R_4$ is equal to 56%, cleaning water is supplied to the substrate surface, and then, development is stopped.

The procedures from step S103 to S107 will be described below.

In the following Table 2, there are shown space ratios $r_i$ of each layer in order from the minimum sum of squares to the reflectance measurement value when 20 seconds elapse after development starts.

TABLE 2

| Rank | Layer $R_1$ 25 nm | Layer $R_2$ 135 nm | Layer $R_3$ 135 nm | Layer $R_4$ 5 nm | Layer $D_1$ 10 nm | Layer $D_2$ 10 nm | Sum of squares |
|---|---|---|---|---|---|---|---|
| 1 | 0.60 | 0.60 | 0.60 | 0.60 | 1.00 | 1.00 | 0.115 |
| 2 | 0.60 | 0.60 | 0.60 | 0.60 | 0.95 | 1.00 | 0.119 |
| 3 | 0.50 | 0.50 | 0.50 | 0.60 | 1.00 | 1.00 | 0.120 |
| 4 | 0.50 | 0.50 | 0.50 | 0.60 | 0.95 | 1.00 | 0.123 |
| 5 | 0.60 | 0.60 | 0.60 | 0.60 | 0.90 | 1.00 | 0.126 |
| 6 | 0.50 | 0.50 | 0.50 | 0.60 | 0.90 | 1.00 | 0.129 |
| 7 | 0.50 | 0.50 | 0.60 | 0.60 | 1.00 | 1.00 | 0.130 |
| 8 | 0.60 | 0.60 | 0.60 | 0.60 | 0.95 | 0.95 | 0.130 |
| 9 | 0.50 | 0.50 | 0.50 | 0.60 | 0.95 | 0.95 | 0.133 |
| 10 | 0.50 | 0.60 | 0.70 | 0.70 | 1.00 | 1.00 | 0.134 |

If the best matching space ratio is extracted as is in the conventional method, layers $R_1$ to $R_4$ each have the developer space ratio of 0.6, and layers $D_1$ and $D_2$ each have the developer space ratio of 1.00. In this case, the difference is slightly 4% between the sum of squares in ranks 1 and 2. The difference is within an error range considering the margin of the ratio (allowable range value: 10%). Therefore, the sum of squares ranging within 10% of the sum of squares in the rank 1 is given as a candidate. The space ratio predictive value $rp_i$ is calculated from the ratio of developer occupying space based on weighted average. In the Table 2, ranks 1 to 5 are given as the candidate. The result of an experiment is shown in the following Table 3.

TABLE 3

| | Layer $R_1$ 25 nm | Layer $R_2$ 135 nm | Layer $R_3$ 135 nm | Layer $R_4$ 5 nm | Layer $D_1$ 10 nm | Layer $D_2$ 10 nm |
|---|---|---|---|---|---|---|
| Ratio of resist | 0.560 | 0.560 | 0.560 | 0.600 | 0.961 | 1.000 |

According to the result, the bottom dimension of the resist in this stage was determined as 114.4 nm (=260×(1−0.56). A desired pattern dimension is 115 nm±8%; therefore, development was stopped in the stage, and rinsing was carried out. To make sure, a comparison by the database prepared under the same condition as the Table 1 in atmosphere was made; as a result, the resist remaining pattern dimension was 114.0 nm. In this case, developer/space is replaced with atmosphere/space, and modeling is carried out using optical constant of atmosphere. Further, a length measuring machine using an electron beam measured the line width of the resist pattern. As a result, the resist pattern was 114.1 nm, that is, the same value as the developing measurement value was obtained.

Figure 5:
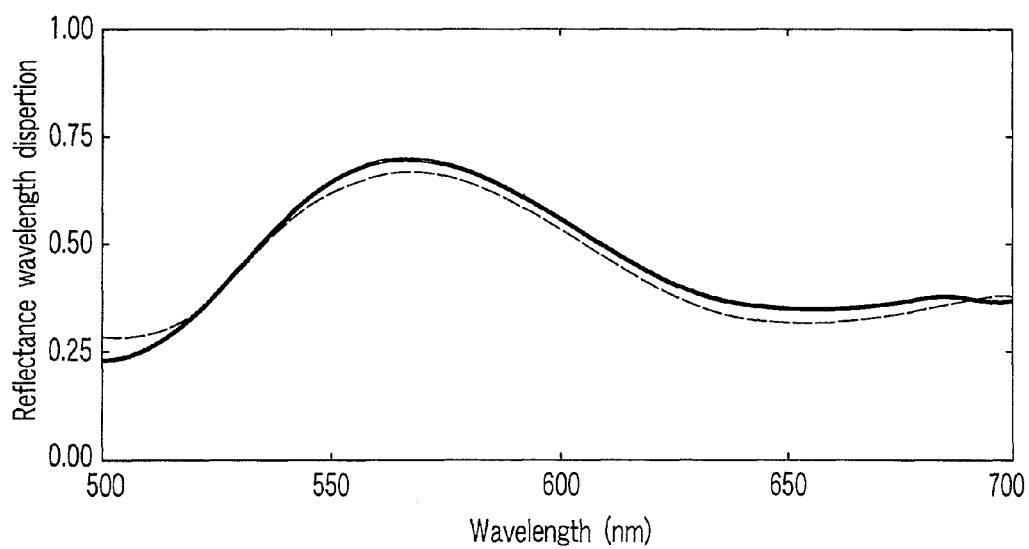
FIG. 5 is a graph to explain a comparison between a calculated reflectance and a measured value.

In FIG. 5, there is shown a comparison between a reflectance calculated using the space ratio predictive value calculated based on the foregoing weighted average and a measured value. FIG. 5 shows the comparison in a range from 500 nm to 700 nm. In FIG. 5, there is shown the solid line curve fitting the measured value using a 15-order function. It can be seen that the calculated reflectance wavelength dispersion using the distribution shown in the Table 3 is very weighted in the 15-order function. Therefore, the actual measured value is sufficiently reproduced.

In FIG. 5, reflectance wavelength dispersion calculated from the minimum sum of squares model is shown by the broken line. The curves shown by the solid and broken lines locally coincide with each other. However, it is difficult to say that these curves coincide with each other in the entire wavelength range shown in FIG. 5. In addition, the measured resist pattern line width is 104 nm, which is 10 nm thinner than the actual value. With the measured value, the resist pattern is determined as failure; as a result, the substrate is reclaimed. The foregoing 114 nm is a true value, and thus, the result of making an incorrect determination as to whether a product is defective or not is given as a matter of course.

According to the first embodiment, it is possible to predict the dimension more accurately than the conventional method. In addition, it is possible to make a suitable determination as to whether a produce is defective or not. The following Table 4 shows model conditions in the case where analysis having the same accuracy as the present experiment is made using the conventional method.

TABLE 4

| Film structure | Classification of film structure | Range of ratio | Step of ratio (%) |
|---|---|---|---|
| Developer layer | Layer $D_2$ | Developer/space = ratio of layer $D_1$ - 1.00 | 0.01 |
| | Layer $D_1$ | Developer/space = 0.80-1.00 | 0.01 |
| Resist layer | Layer $R_4$ | Developer/space = ratio of layer $R_3$ - 1.00 | 0.01 |
| | Layer $R_3$ | Developer/space = ratio of layer $R_2$ - 0.70 | 0.01 |
| | Layer $R_2$ | Developer/space = ratio of layer $R_1$ - 0.70 | 0.01 |
| | Layer $R_1$ | Developer/space = 0-0.70 | 0.01 |
| Anti-reflection film layer | Anti-reflection film layer | Anti-reflection material/space = 1.00 (fixed) | — |
| Si substrate | Si substrate | Si/space = 1.00 (fixed) | — |

The number of calculated values prepared in the Table 1 is $1/2.5 \times 10^5$ of that of the Table 4; therefore, the number of data is largely reduced. The detection time is 0.2 seconds, and measurement in developing is readily made. According to the conventional method, about 14 hours are taken to make the measurement. As a result, it is considerably difficult to apply the conventional method to the measurement in developing. In addition, it is difficult to apply the conventional method to evaluation in normal atmosphere. As seen from the foregoing description, retrieval time is largely shortened, and the resist pattern dimension is readily predicted in accordance with the advance of the process.

Figure 6:
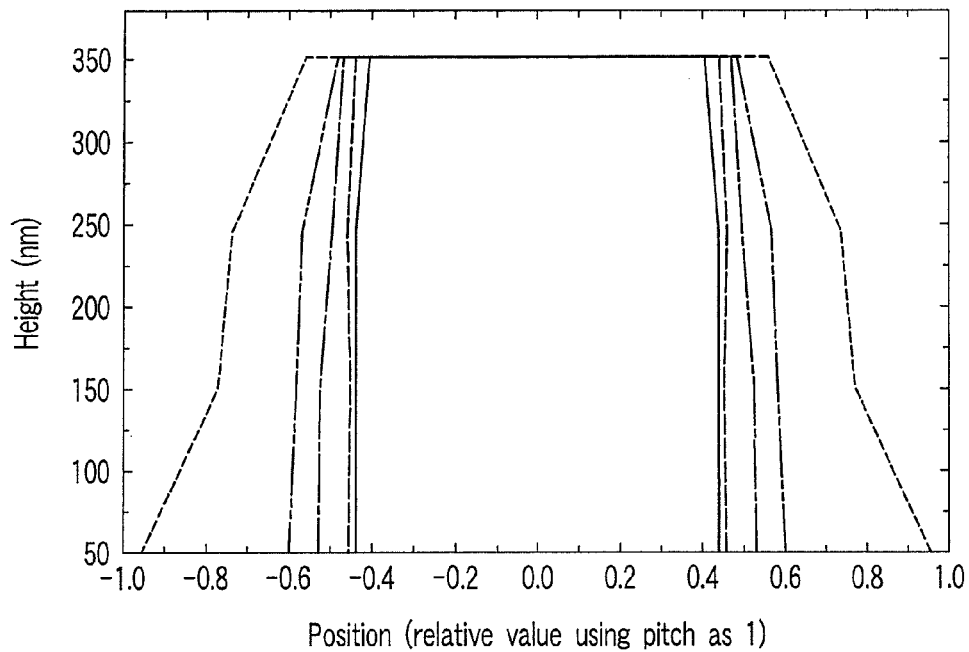
FIG. 6 is a chart showing the dimensional variable result of a developing KrF resist using a sectional shape.

The resist pattern dimension is predicted in the first embodiment. The present invention, however, is not limited to the preceding embodiment. FIG. 6 is a graph showing dimension variations of developing KrF resist in sectional shapes using the reflectance wavelength dispersion calculation value database calculated based on the model of the Table 1. The sectional shapes are obtained by calculating a ratio of resist to space for each layer, and connecting the calculated ratios in the film thickness direction. In FIG. 6, a dotted line shows a sectional shape of the resist pattern after 4 seconds from the development start. A chain double-dashed line shows a sectional shape of the resist pattern after 6 seconds from the development start. A chain dashed line shows a sectional shape of the resist pattern after 10 seconds from the development start. A rough dashed line shows a sectional shape of the resist pattern after 20 seconds from the development start. A solid line shows a sectional shape of the resist pattern after 30 seconds from the development start. It can be seen that the bottom dimension of the resist pattern is wide after 4 seconds from the development start. With the advance of development, the resist pattern becomes gradually thin in its top and bottom, and then, is formed into a rectangular shape.

Figure 7:
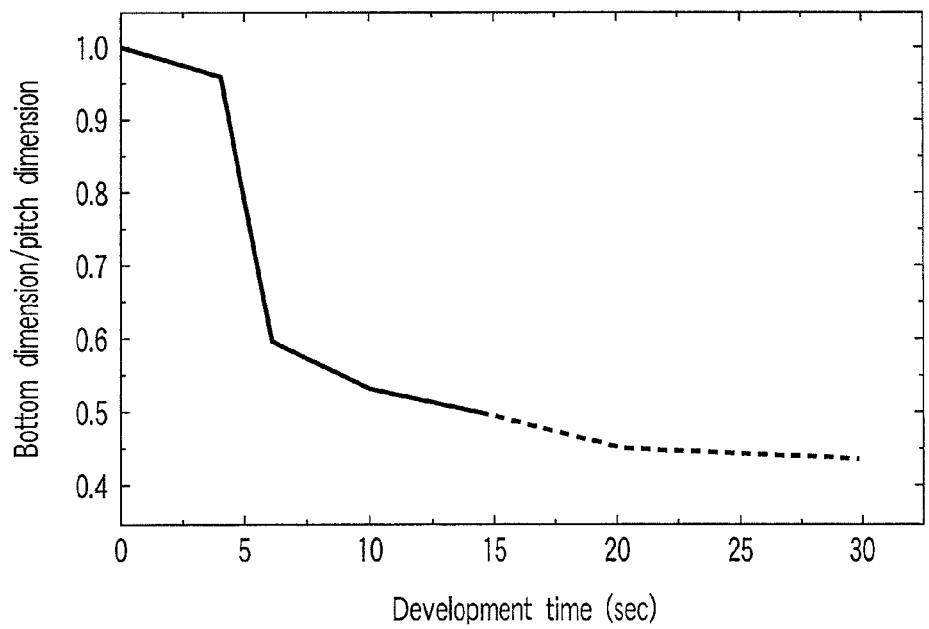
FIG. 7 is a graph to explain the relationship between development time and a bottom dimension.

FIG. 7 is a graph showing the bottom dimension of the resist film with development time as the horizontal axis. FIG. 7 exhibits that the time when the resist pattern becomes a 0.44 size to pitch is 20 seconds (dashed line denotes a dimension ratio calculated without stopping development). As shown in FIG. 7, the dimension with respect to time is calculated one after another to predict development time to obtain a desired dimension. The development is stopped, and thereby, high-accurate development control is possible. FIG. 6 is obtained from calculation based on weighted average using several reflectance wavelength dispersion calculation values. Therefore, the relationship shown in FIG. 7 has high accuracy.

Figure 8:
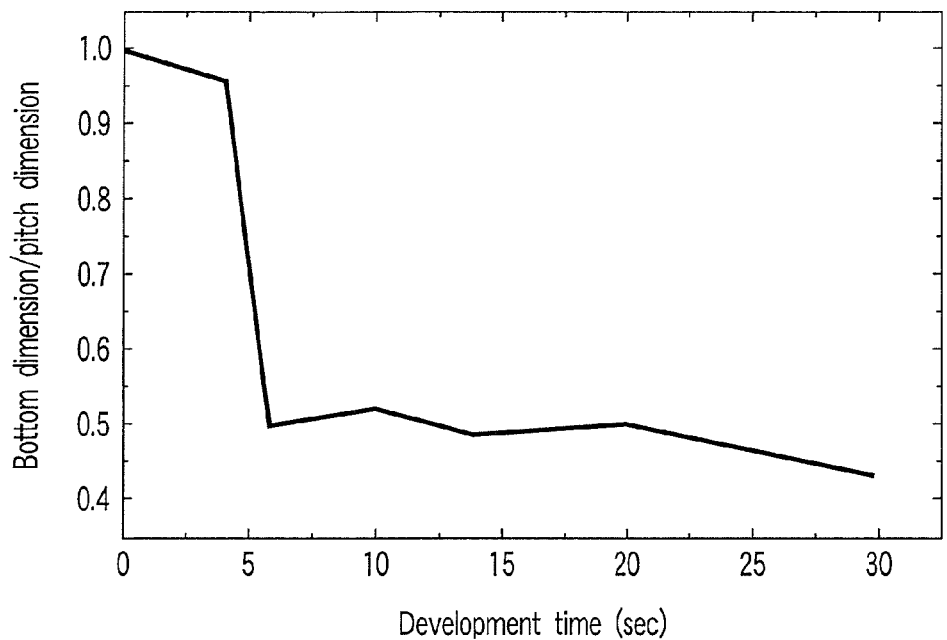
FIG. 8 is a graph to explain the relationship between development time and a bottom dimension obtained from a conventional method.

On the contrary, according to the conventional method, the dimension ratio relationship with respect to development time is reversed as seen from FIG. 8; for this reason, accurate development control is not obtained. Consequently, the method of this embodiment is employed, and thereby, it is possible to greatly improve the development control.

The first embodiment relates to dimension measurement in development and after development; however, the present invention is not limited to this embodiment. For example, the present invention is applicable to dimension measurement for etching pattern of oxide film and interconnection pattern. In this case, database and measured values are analyzed in the same method as the resist pattern dimension measurement. The database comprises materials such as oxide film and interconnection and reflectance wavelength dispersion calculation values calculated by changing the space ratio. By doing so, it is possible to effectively obtain the pattern dimension and profile with high accuracy for short time.

The first embodiment relates to structure prediction using reflectance calculation; however, the present invention is not limited to this embodiment. For example, cos δ and tan ψ are calculated by RCWA from film structure models which have several space ratios to prepare database. Then, similar waveforms as cos δ and tan ψ measured by ellipsometry technique are found from the database using the similar method described above. The space ratio is predicted based on weighted average where larger weight is given as the error is smaller. By doing so, it is possible to specify the structure of the measured substance.

In the first embodiment, the space ratio predictive value r is calculated based on the weighted average using reciprocals of the sum of squares as shown in the equation (4). However, the present invention is not limited to the calculation. The space ratio predictive value r may be calculated using any other equations so long as the space ratio is large when R, which is an absolute value R of an error of a measured value, is small. For example, the space ratio predictive value r is expressed using the following equation (5). The f(R) in the equation (5) should decreases as R increases in a range R can take, that is f(R) should be simple decreasing function in a range R can take.

$$r=(\Sigma r_i \times f(F))/(\Sigma f(R)) \tag{5}$$

where, $f(R)=1/R$, $1/R^x$: x is positive real number, $e^{-R}$, etc.

(2) Second Embodiment

An etching depth is calculated in the same manner as the first embodiment. More specifically, etching pattern materials and a space ratio of etching atmosphere (supply gas and reaction gas) are changed, and a reflectance wavelength dispersion calculation value database is prepared. Measured values are compared with the database to extract several wavelength dispersion calculation values similar to these measured values. The etching depth is calculated from weighted average based on the sum of squares of the original space ratio.

Figure 9:
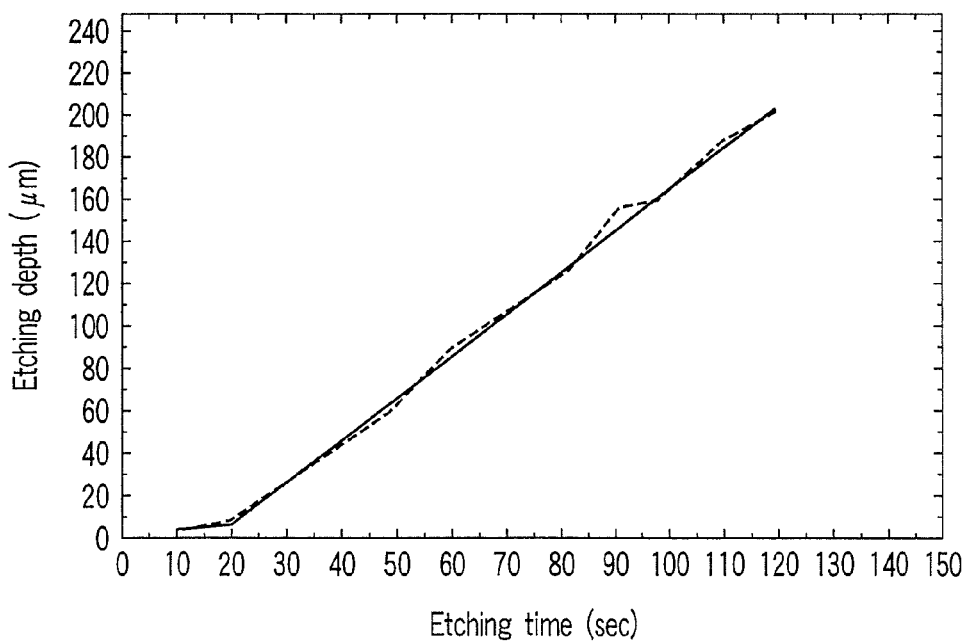
FIG. 9 is a graph to explain the relationship between etching time and etching depth according to a second embodiment of the present invention.

FIG. 9 is a graph showing etching depth calculated from reflectance measured for each etching time of oxide film. The depth (dashed line) calculated by the conventional method has a large drift of etching rate as time passes; as a result, the calculated depth is unstable. On the contrary, the etching depth (solid line) to etching time calculated based on weighted average according to the present embodiment is very favorable. A constant value is obtained in the etching rate after 20 seconds (i.e., a change of the etching depth to unit etching time is constant). Thus, in the second embodiment, etching depth analysis is carried out without receiving an influence by analysis error.

Etching stop control is possible using FIG. 9. However, the conventional method has the following problem. The drift is large, and etching stop accuracy worsens; for this reason, the stopper film under the oxide film may be etched. On the contrary, according to the method of the second embodiment, etching stop control is possible with high accuracy. Therefore, fine processing is realized without giving damages to the stopper material under the oxide film; as a result, the process of forming the stopper film is largely reduced.

(3) Third Embodiment

The third embodiment relates to a structure inspection method of films in a process of manufacturing a semiconductor device.

[3-1] Flow of the Process of Manufacturing a Semiconductor Device

Figure 10:
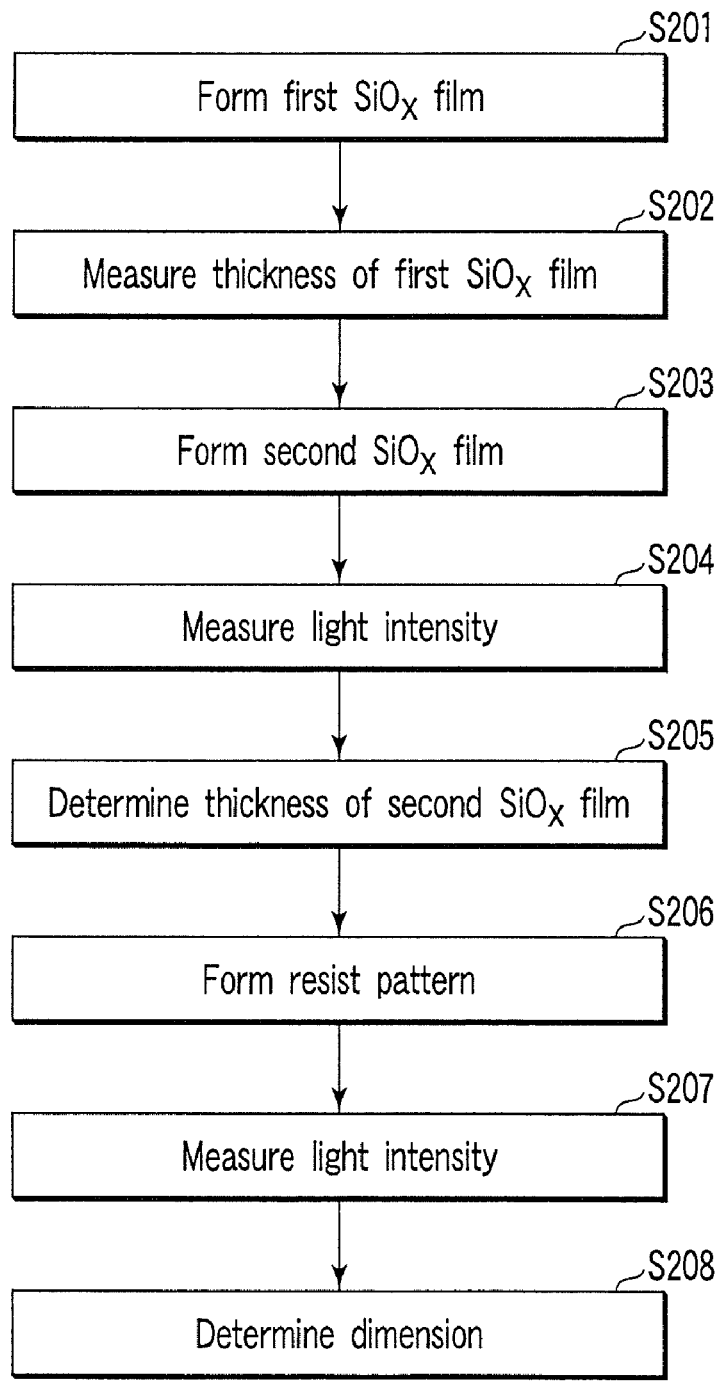
FIG. 10 is a flowchart to explain the process of manufacturing a semiconductor device according to a third embodiment of the present invention.

The process of manufacturing a semiconductor device will be described below with reference to FIG. 10 to FIG. 12. FIG. 10 is a flowchart to explain the process of manufacturing a semiconductor device according to the third embodiment of the present invention. FIGS. 11A to 11C are each cross-sectional views successively showing the process of manufacturing a semiconductor device according to the third embodiment.

Figure 11A:
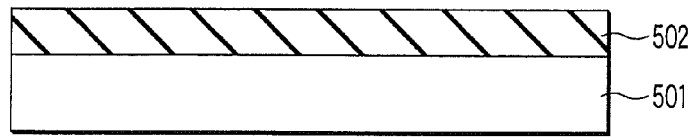
FIGS. 11A, 11B and 11C are each cross-sectional views successively showing the process of manufacturing a semiconductor device according to the third embodiment.
Figure 12:
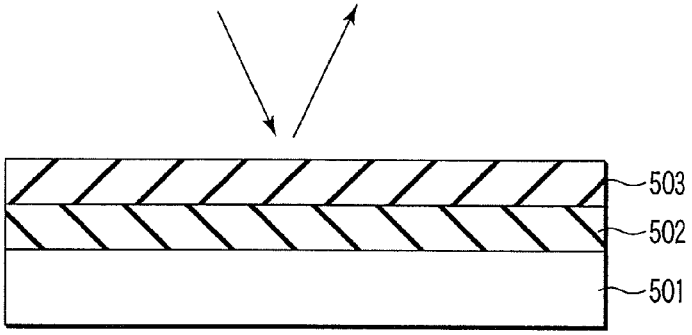
FIG. 12 is a schematic view showing a substrate A and a light intensity measurement optical system.

As shown in FIG. 11A, a first silicon oxide film 502 having a film thickness of 100 nm is formed on a non-processed silicon substrate 501 (step S201). Thereafter, the film thickness of the silicon oxide film 502 is measured (step S202).

Figure 11B:
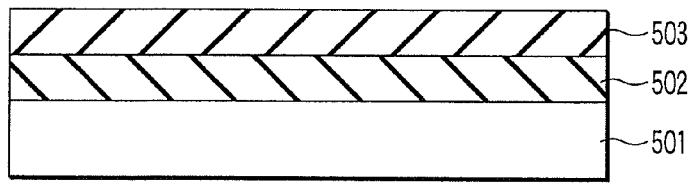

As illustrated in FIG. 11B, a second silicon oxide film 503 having a film thickness of 500 nm is formed on the first silicon oxide film 502 (step S203). The first and second silicon oxide films 502 and 503 have optical constant slightly different from each other. The substrate formed with the second silicon oxide film 503 is called a substrate A.

In order to measure the film thickness of the second silicon oxide film 503, the light intensity of the substrate A (step S204) is measured. FIG. 12 is a schematic view showing a light intensity optical system. Light travels into the substrate A. A reflected light from the substrate A is measured, and thereby, wavelength dispersion of intensity change (tan ψ) and phase change (cos Δ) of the reflected light are measured. TM, TE polarized lights and polarized light beam such as other polarized lights may be used as the reflected light measured here, or reflected light may be directly used without using a deflection plate. Incident angle may be vertical to the substrate A. Light of single wavelength may be used, and then, incident angle and detection angle are changed to measure the intensity. In brief, any method can be taken as long as reflected incident light is measured.

The film thickness of the second silicon oxide film 503 is determined from the measured light intensity of the substrate A (step S205).

Figure 11C:
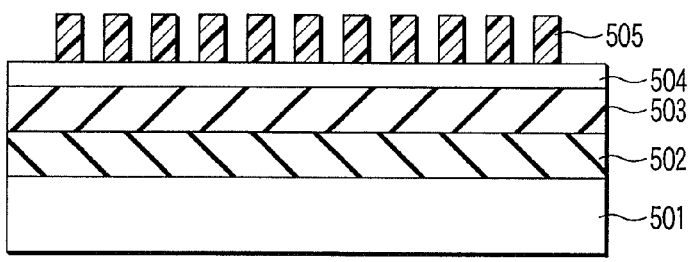

As depicted in FIG. 11C, an anti-reflection film 504 having a film thickness of 50 nm and a resist film 505 of 250 nm are coated and formed on the second silicon oxide film 503 (step S206). The resist film 505 is exposed using ArF excimer laser via reticle. Baking and development are carried out; as a result, a resist pattern having 100 nm line/space (1:1) is formed. The resist pattern has lines and spaces which have a width of 100 nm and are arranged alternatively. The substrate of the foregoing state is called a substrate B.

Figure 13:
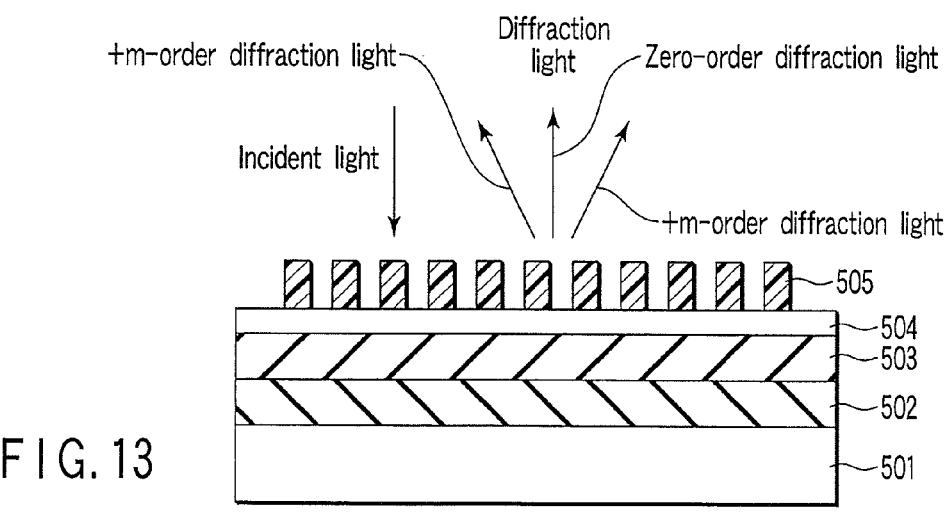
FIG. 13 is a schematic view showing a substrate B and a light intensity measurement optical system.

In order to measure the film thickness of the anti-reflection film 504, the pattern dimension and film thickness of the resist film 505, light intensity of the substrate B is measured (step S207). FIG. 13 is a schematic view showing an optical system used for the process of inspecting the substrate B. Light is radiated to the substrate B. Zero-order light of diffraction lights from the substrate B is measured, and thereby, the wavelength dispersion of intensity change (tan ψ) and phase change (cos Δ) of the diffraction light are measured. TM, TE polarized lights and polarized light beam such as other polarized lights may be used as the measurement target, or diffraction light may be directly used without using a deflection plate, like the film thickness measurement. In addition, first-order or more light may be used instead of the zero-order light. Vertical or oblique incident angle may be used as the incident angle of light. Light is made incident on the substrate B at single wavelength, and then, incident angle and detection angle are changed to measure the intensity. In brief, any method can be taken as long as reflected incident light is measured.

The resist pattern dimension (line width) is measured from the light intensity of the substrate B as the inspection for anti-reflection film 504 and resist pattern (step S208). In semiconductor wafer process, processes and the inspection of structure (film thickness, pitch, ratio, dimension, optical constant) changed or added by the process are repeatedly carried out.

[3-2] Inspection Procedure

Figure 14:
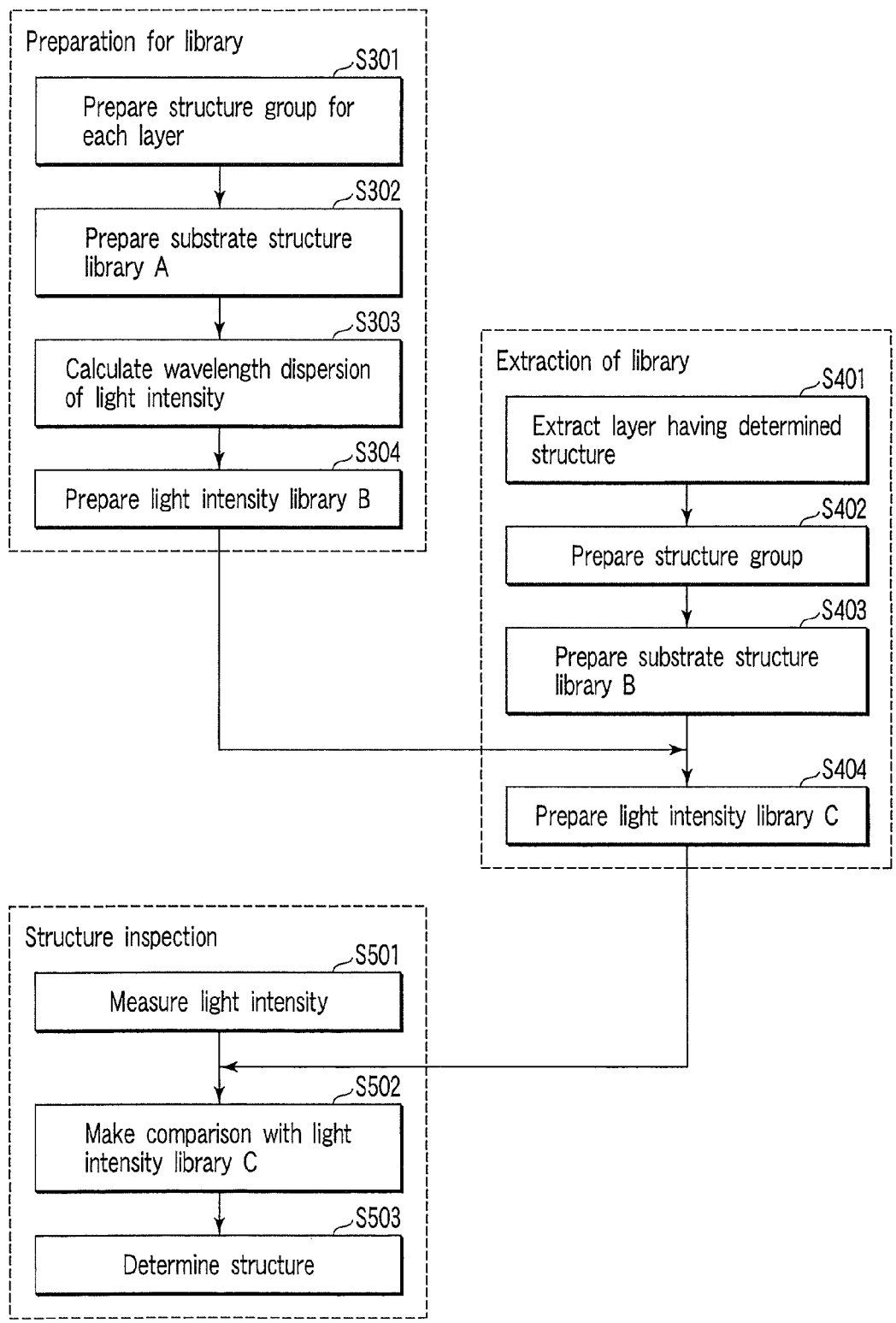
FIG. 14 is a flowchart to explain the structure inspection procedure according to the third embodiment.

The inspection procedure will be explained in detail below. FIG. 14 is a flowchart to explain the structure inspection procedure according to the third embodiment. Prior to inspection, a light intensity library storing substrate structure and light intensity corresponding thereto is prepared.

A structure group including structures predicted in at least each layer is prepared with respect to all layers on the substrate (step S301). Layer structure is optical constant of layer, film thickness, pitch, ratio, dimension, etc. Predicted layer structure is included in a range of structure variations occurring in process. A substrate structure is prepared by combining structures of each layer.

A substrate structure library A comprising various substrate structures prepared in step S301 is prepared (step S302). Light is irradiated to each substrate structure stored in the substrate structure library A under the same condition as the actual inspection. Thus, light intensity obtained by reflection or diffraction is calculated, and further, wavelength dispersion of the light intensity in each substrate structure is calculated (step S303). In general, RCWA (Rigorous coupled-wave analysis) by Morham et al. (J. Opt. Soc. Am., Vol. 12, No. 5, May 1995 1077-1086) is used as the calculation method. According to the foregoing RCWA, electric filed, magnetic field and intensity of refraction light from regular pattern are obtained using Maxwell equations.

A light intensity library B is prepared (step S304). The light intensity library B stores substrate structures stored in the substrate structure library A and wavelength dispersion of light intensity corresponding thereto.

Prior to structure inspection, the inspection result of structure actually prepared in the manufacture process is used, and thereby, light intensity library is extracted (narrowed down). In the extraction, substrate structures including structures diverging from already-existing structures obtained by inspection are removed from the inspection comparison target. By doing so, it is possible to reduce the number of comparison target substrate structures stored in library in the comparison process between substrate structures in inspection target and library. Namely, layers having the layer structure determined by actual inspection (e.g., structure-inspected layers under inspection target layer) are extracted (step S401). Then, a layer structure group is prepared with respect to the extracted layer based on the layer structure inspection result (step S402). In this case, the layer structure group is prepared considering inspection accuracy.

The structure group of the extracted layer is compared with the substrate structure library A prepared in step S302. By doing so, substrate structures including the structure group of the extracted layer are extracted. As a result, a substrate structure library B is prepared (step S403).

Light intensity corresponding to substrate structures in the substrate structure library B is fetched from the light intensity library B. By doing so, a light intensity library C is prepared (step S404).

Substrates having actual several layers on it are carried into the inspection apparatus having the optical system shown in FIG. 2 and FIG. 3. Thereafter, wavelength dispersion of the light intensity in the inspection area is measured (step S501). Wavelength dispersion of the measured light intensity is compared with wavelength dispersion stored in the light intensity library C (Step S502). The wavelength dispersion which matches best with the wavelength dispersion of the measured light intensity is detected from the light intensity library C. The substrate structure corresponding to the detected wavelength dispersion is determined as an inspection target substrate structure (step S503).

For comparison, the conventional inspection procedure will be described below with reference to FIG. 18. As seen from FIG. 18, the light intensity library B based on the inspection result of already-obtained layers is not prepared in the conventional inspection procedure unlike the second embodiment. In other words, the light intensity library A is compared with the light intensity measured result (step S512).

[3-3] Another Embodiment of Inspection Procedure

Figure 15:
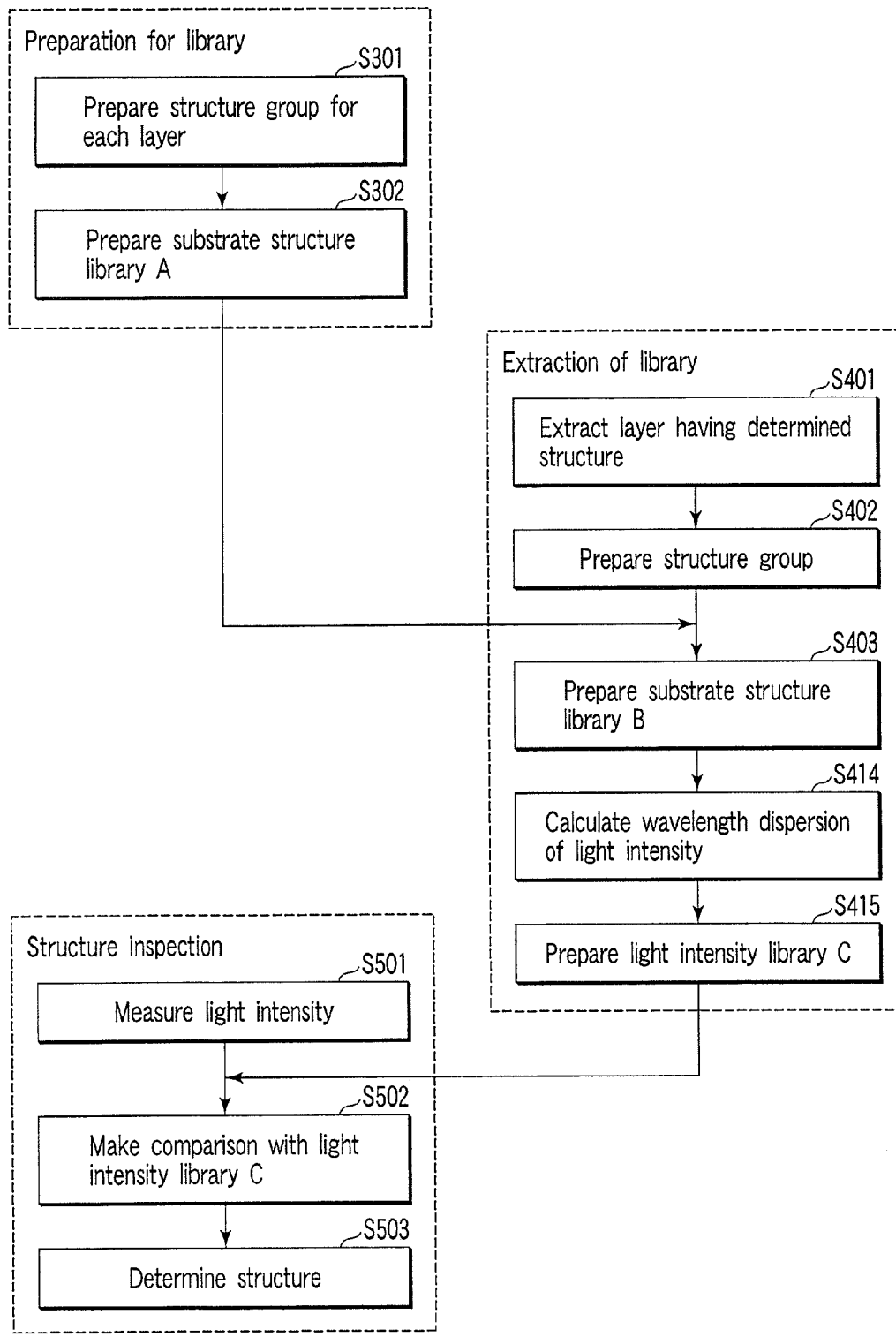
FIG. 15 is a flowchart to explain the structure inspection procedure according to the third embodiment.

Various methods may be given as the procedure of preparing the light intensity library C. The procedure shown in FIG. 15 is given as one of these methods. According to the inspection procedure shown in FIG. 15, no wavelength dispersion calculation of light intensity of substrate structures stored in the substrate structure library A is made. Instead of that, wavelength dispersion of light intensity of each substrate structure is calculated after the substrate structure library B (step S414). By doing so, a light intensity library C is prepared (step S415).

Figure 16:
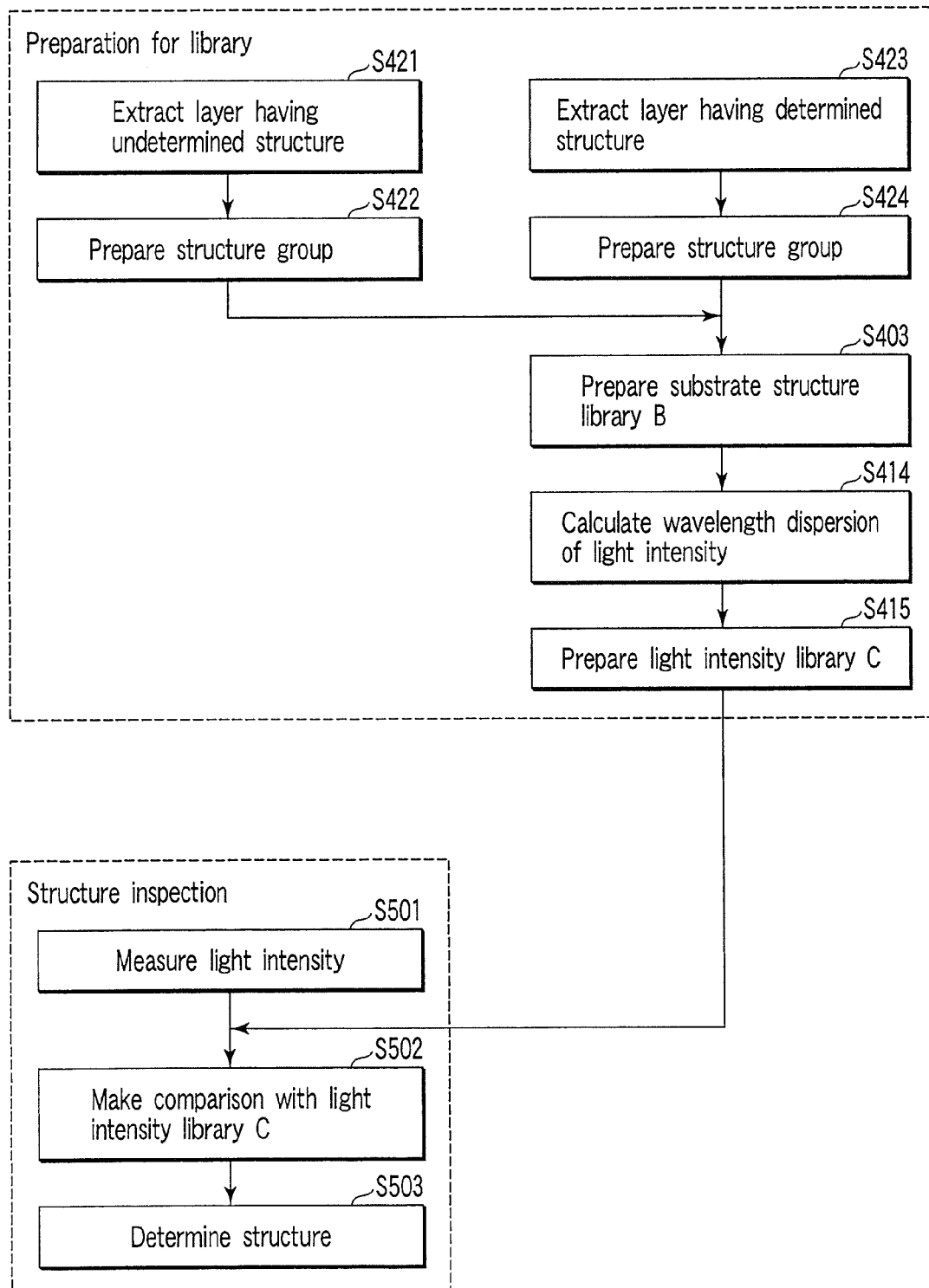
FIG. 16 is a flowchart to explain the structure inspection procedure according to the third embodiment.

The procedure taken according to a flowchart shown in FIG. 16 is given as another embodiment of the present invention. According to the inspection procedure shown in FIG. 16, a layer having no determined structure (e.g., layer which has undergone no structure inspection because the structure is not determined) is extracted in detecting a substrate structure of a certain state (step S421). Thereafter, a structure group relevant to the layer extracted in step S421 is prepared (step S422).

In addition, a structure-determined layer (e.g., actually formed layer already having undergone structure inspection) is extracted (step S423). Thereafter, a structure group of the structure-determined layer is prepared (step S424). A substrate structure library B is prepared based on the structure groups prepared in steps S422 and S424 (step S403). In other words, various structures are formed by putting the predicted structures on structure-inspected layers. The structures obtained like this makes the substrate structure library B.

Figure 17:
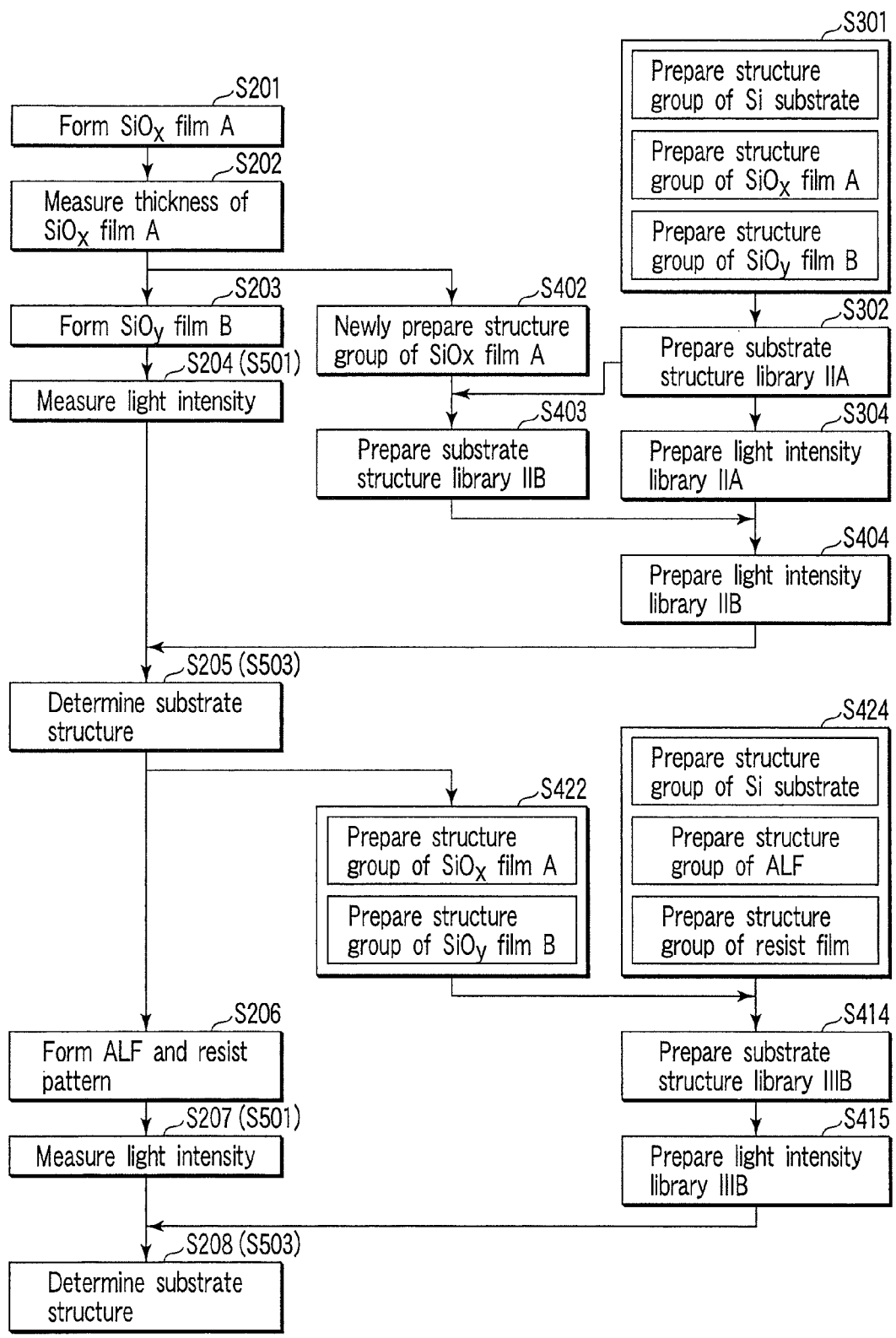
FIG. 17 is a flowchart to explain the process of manufacturing a semiconductor device according to the third embodiment of the present invention.

[3-4] Process of Manufacturing a Semiconductor Device Including Inspection Process An example of embodiment in which the inspection procedure described with reference to FIG. 11A to FIG. 11C is applied to the process of manufacturing the semiconductor device will be described. FIG. 17 is a flowchart to explain the process of manufacturing a semiconductor device according to the third embodiment of the present invention. When the light intensity is measured (step S204), silicon oxide films A and B (first and second silicon oxide films) are formed on the Si substrate. Therefore, a substrate structure library IIA includes each predicted structure group of the foregoing Si substrate, silicon oxide films A and B (step S301). The substrate structure library IIA was prepared using each structure group prepared in step S301 (step S302). The number of structure groups of the Si substrate, silicon oxide films A and B prepared in step S301 were 1, 21 and 101, respectively. Thus, the number of structure groups stored in the substrate structure library IIA was 2121.

A structure group of the silicon oxide film A is newly prepared using the film thickness of the silicon oxide film measured in step S202 (step S402). In other words, a structure group including the actually formed silicon oxide film A is prepared. The film thickness $d_A$ of the silicon oxide film was determined as 102 nm, and the measurement accuracy was set as ±1 nm in an experiment. Thus, a structure group of the silicon oxide film A shown in the following Table 5 was prepared. The allowable range value of the film thickness was set to 1 nm in order to improve the measurement accuracy

TABLE 5

| Layer | Refractive index | Extinction coefficient | Allowable range of film thickness | Step | Number of structures |
|---|---|---|---|---|---|
| Si substrate | $n_0$ | $k_0$ | — | — | 1 |
| Silicon oxide film A | $n_1$ | $k_1$ | $d_A \pm 1\%$ | 1 nm | 3 |
| Silicon oxide film B | $n_2$ | $k_2$ | $d_B \pm 1\%$ | 1 nm | 101 |

Therefore, in the substrate structure library IIA, necessary substrate structure is combinations of structure groups shown in the Table 5. As a result, the number of structures of Si substrate, silicon oxide films A and B prepared in step S403 are 1, 3 and 101, respectively. Thus, a substrate structure library IIB was composed of substrate structures comprising these combinations. Wavelength dispersion of the light intensity corresponding to each substrate structure stored in the substrate structure library IIB is extracted from the light intensity library IIA. By doing so, a light intensity library IIB is prepared. Therefore, the number of wavelength dispersions of the light intensity stored in the light intensity library IIB prepared in step S404 was 303.

When the wavelength dispersion of light intensity in step S207 is measured, silicon oxide films A, B, anti-reflection film (ALF) and resist film are formed. Each structure group is prepared from predicted structures of the foregoing silicon oxide films A, B, anti-reflection film (ALF) and resist film. In this case, each structure of the silicon oxide films A and B was detected in steps S202 and S205. Thus, based on the detection result, each structure group of the silicon oxide films A and B was prepared (step S422). In addition, each structure group of Si substrate, anti-reflection film and resist film having undergone no structure detection is prepared based on predicted several structures (step S424).

The film thickness $d_A$ of the silicon oxide film A was determined as 102 nm, and the film thickness $d_B$ of the silicon oxide film A was determined as 510 nm, and further, the measurement accuracy was set as ±1 nm. Therefore, each structure group of the silicon oxide films A and B shown in the following Table 6 is prepared. These structure groups are combined, and thereby, various substrate structures are obtained; therefore, a substrate structure library IIIB was prepared based on these substrate structures. In the Table 6, each structure group of Si substrate, anti-reflection film and resist film is shown.

TABLE 6

| Layer | Refractive index | Extinction coefficient | Allowable range of film thickness | Step | Allowable range of dimension | Step | Number of structures |
|---|---|---|---|---|---|---|---|
| Si substrate | $n_0$ | $k_0$ | — | — | — | — | 1 |
| Silicon oxide film A | $n_1$ | $k_1$ | $d_A \pm 1\%$ | 1 nm | — | — | 3 |

TABLE 6-continued

| Layer | Refractive index | Extinction coefficient | Allowable range of film thickness | Step | Allowable range of dimension | Step | Number of structures |
|---|---|---|---|---|---|---|---|
| Silicon oxide film B | $n_2$ | $k_2$ | $d_B \pm 1\%$ | 1 nm | — | — | 11 |
| Anti-reflection film | $n_3$ | $k_3$ | $d_3 \pm 2\%$ | 1 nm | — | — | 3 |
| Resist film | $n_4$ | $k_4$ | $d_4 \pm 2\%$ | 1 nm | $w_4 \pm 10\%$ | 1 nm | 231 |

As depicted in the Table 6, the substrate structure library IIIB stores substrate structures obtained from the combination of structure groups shown in the Table 6. The number of each structure group of silicon oxide films A, B, Si substrate, anti-reflection film and resist film were 1, 3, 11, 3, 231, respectively. Therefore, the number of substrate structures stored in the substrate structure library IIIB was 22869. A light intensity library IIIC is prepared from wavelength dispersion of the light intensity corresponding to substrate structures stored in the substrate structure library IIIB.

In preparation for the structure group of silicon oxide films A and B, the structure group was prepared based on a measurement accuracy range (±1%) as seen from the Table 6. The structure group may be prepared based on a measurement accuracy range (±2%) of two times as much as the foregoing definition in view of a margin. In preparation for the structure group of anti-reflection film and resist film, the structure group may be prepared based on a measurement accuracy range (±4%) of two times as much as the foregoing range in view of a margin against drift.

Figure 18:
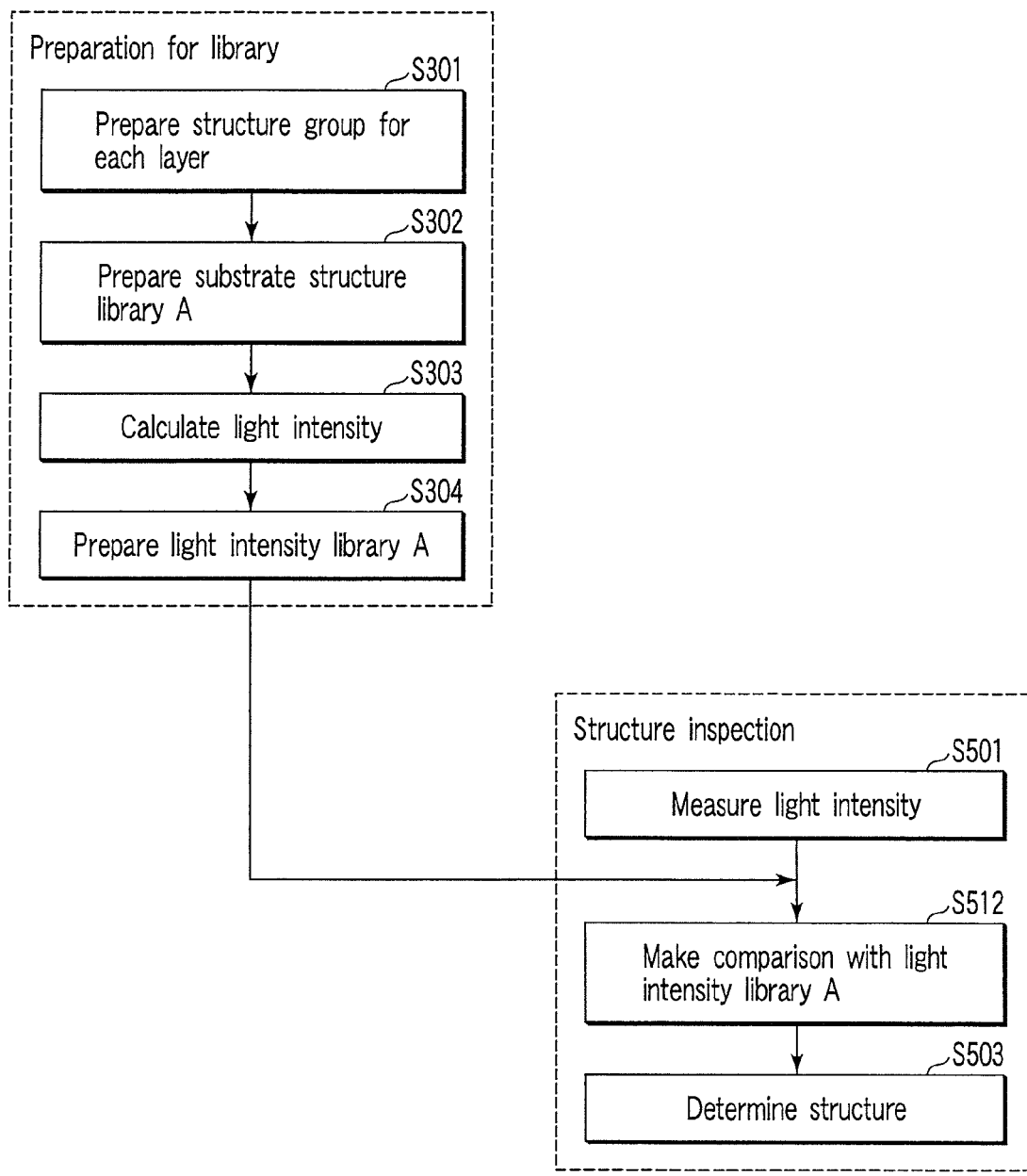
FIG. 18 is a flowchart to explain the conventional structure inspection procedure.
Figure 19:
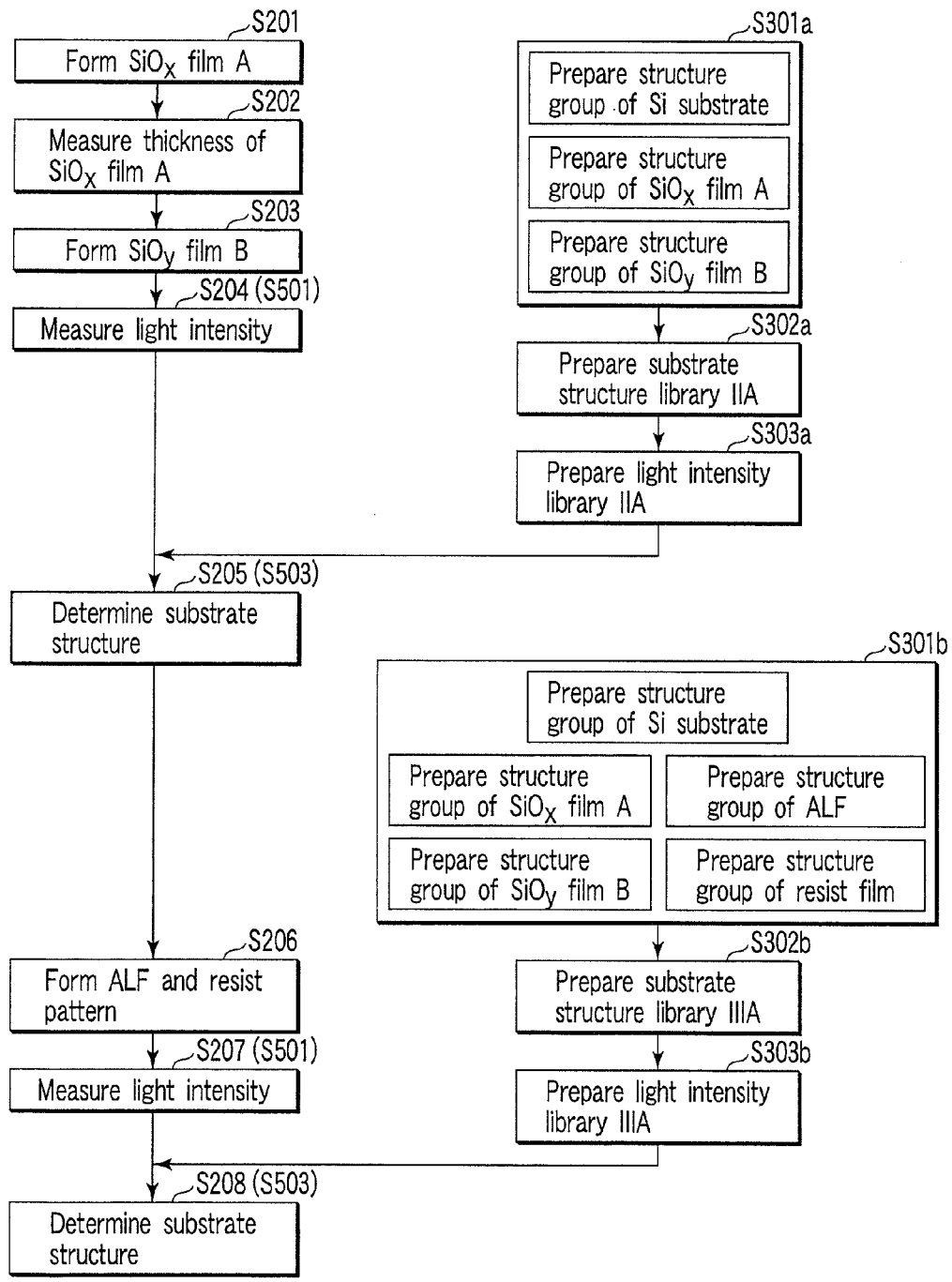
FIG. 19 is a flowchart to explain the process of manufacturing a conventional semiconductor device.

For comparison, the case where the conventional structure inspection method shown in FIG. 18 is applied to the flow shown in FIG. 10 will be described below with reference to FIG. 19. As seen from FIG. 19, according to the conventional method, the light intensity library IIB based on the inspection result of obtained layers is not prepared unlike the third embodiment. For this reason, a comparison is required between the light intensity library IIB and the light intensity measurement result (step S503).

In step S204 of making light intensity measurement for inspecting the structure of the silicon oxide film B, silicon oxide films A and B are formed on the Si substrate. Therefore, each predicted structure group of Si substrate, silicon oxide films A and B was prepared (step S301*a*).

TABLE 7

| Layer | Refractive index | Extinction coefficient | Allowable range of film thickness | Step | Number of structures |
|---|---|---|---|---|---|
| Si substrate | $n_0$ | $k_0$ | — | — | 1 |
| Silicon oxide film A | $n_1$ | $k_1$ | $d_A \pm 10\%$ | 1 nm | 21 |
| Silicon oxide film B | $n_2$ | $k_2$ | $d_B \pm 10\%$ | 1 nm | 101 |

The refractive index and the extinction coefficient have no drift in the process flow of inspecting silicon oxide films A and B. The silicon oxide films A and B each had a film thickness of ±10% with respect to the main value; therefore, a structure group shown in the Table 7 was defined.

As shown in the Table 7, the number of structure groups of Si substrate, silicon oxide films A and B were 1, 21 and 101, respectively. Therefore, the number of substrate structures stored in the light intensity library IIA was 2121 (step S302*a*). The light intensity library IIA was prepared based on the substrate structure library IIA (step S303*a*). For this reason, it stores the same number of wavelength dispersion samples as the substrate structure library IIA.

In step S207 of making light intensity measurement for inspecting anti-reflection film and resist film, silicon oxide films A, B, anti-reflection film and resist film are formed on the Si substrate. Therefore, each predicted structure group of the foregoing Si substrate, silicon oxide films A, B, anti-reflection film and resist film were prepared (step S301*b*).

Each structure group of components described above is shown in the following Table 8.

TABLE 8

| Layer | Refractive index | Extinction coefficient | Allowable range of film thickness | Step | Allowable range of dimension | Step | Number of structures |
|---|---|---|---|---|---|---|---|
| Si substrate | $n_0$ | $k_0$ | — | — | — | — | 1 |
| Silicon oxide film A | $n_1$ | $k_1$ | $d_A \pm 10\%$ | 1 nm | — | — | 21 |
| Silicon oxide film B | $n_2$ | $k_2$ | $d_B \pm 10\%$ | 1 nm | — | — | 101 |
| Anti-reflection film | $n_3$ | $k_3$ | $d_3 \pm 2\%$ | 1 nm | — | — | 3 |
| Resist film | $n_4$ | $k_4$ | $d_4 \pm 2\%$ | 1 nm | $w_4 \pm 10\%$ | 1 nm | 231 |

The refractive index and the extinction coefficient have no drift in the process flow, and the film thickness of silicon oxide film, anti-reflection film and resist film was ±10%, ±2% and ±2% with respect to the center value, respectively. Therefore, a structure group shown in the Table 8 was defined. The number of each structure group of Si substrate, silicon oxide films A, B, anti-reflection film and resist film were 1, 21, 101, 3, 231, respectively. As a result, the number of substrate structures stored in a substrate structure library IIIA defined in step S302$b$ was 453789. A light intensity library IIIA was prepared based on the substrate structure library IIIA (step S303$b$). Thus, the light intensity library IIIA stores the same number of wavelength dispersion samples as the substrate structure library IIIA.

[3-4] Advantages

[3-4-1] Improvement in Measurement Accuracy

The conventional method has the following problems when determining the film thickness of the silicon oxide film B in the structure inspection procedure (step S205). Wavelength dispersions are sometimes almost same in the case where individual film thickness of silicon oxide films A and B are $d_{11}$ nm, $d_{21}$ nm and in the case where individual film thickness of silicon oxide films A and B are $d_{12}$ nm, $d_{22}$ nm. In such a case, individual film thickness of silicon oxide films A and B may be miscalculated as $d_{12}$ nm, $d_{22}$ nm. According to the third embodiment, the value $d_{12}$ is not calculated as the film thickness as long as the value $d_{12}$ is not included in a rage of $d_1$+1% (see FIG. 9). Therefore, an erroneous measurement is unlikely, that realizes an improved measurement accuracy.

[3-4-2] Large Reduction of the Number of Samples Stored in Library

According to the conventional method, the substrate structure library comprising samples including all structural combinations predicted in each layer is prepared and the light intensity library comprising the same number of samples stored in the substrate structure library is prepared. For this reason, the light intensity library stores huge number of samples. On the contrary, according to the third embodiment, the inspection result prior to the inspection in a certain structure inspection process is considered to prepare the light intensity library. Therefore, the number of samples stored in the light intensity library largely decreases. As a result, it is possible to shorten time to retrieve similar wavelength dispersions of light intensity as the measured result of the wavelength dispersions of light intensity.

The following Table 9 shows the number of samples stored in each light intensity library.

|  | Light intensity library IIA | Light intensity library IIB |
| --- | --- | --- |
| Number of samples | 2121 | 303 |
|  | Light intensity library IIIA | Light intensity library IIIB |
| Number of samples | 453789 | 22869 |

According to the conventional method, the substrate structure is determined using light intensity libraries IIA and IIIA. On the contrary, according to the third embodiment, the substrate structure is determined using light intensity libraries IIB and IIIB.

The number of samples stored in the light intensity library is largely reduced, and thereby, the inspection procedure can be taken without preparing additional light intensity library as seen from FIG. 15 and FIG. 16. For example, it is needed to prepare the substrate structure library IIIA and the light intensity library IIIA covering all possible predicted structural combination before the inspection process as preparation for the structure determining process (step S208).

On the contrary, according to the third embodiment, it is not required to prepare the light intensity library IIIA. After the substrate structure is determined (step S205), the light intensity library IIIB reflecting the substrate structure result is prepared. The substrate structure library IIA having all possible samples is not prepared; therefore, the capacity of the library is largely reduced.

When a conventional coater/developer has a structure inspection function, the structure inspection may be made until the process for a series of lots is completed. Thus, it suffices that the light intensity library IIIB is prepared until a series of processes is completed, and the measured light intensity is compared with the light intensity library IIIB to obtain the inspection result. As a result, the capacity of the library is largely reduced while inspection is made with high accuracy.

(4) Fourth Embodiment

The fourth embodiment relates to a pattern evaluation method in development.

[4-1] The Entire Flow of Development

Figure 21:
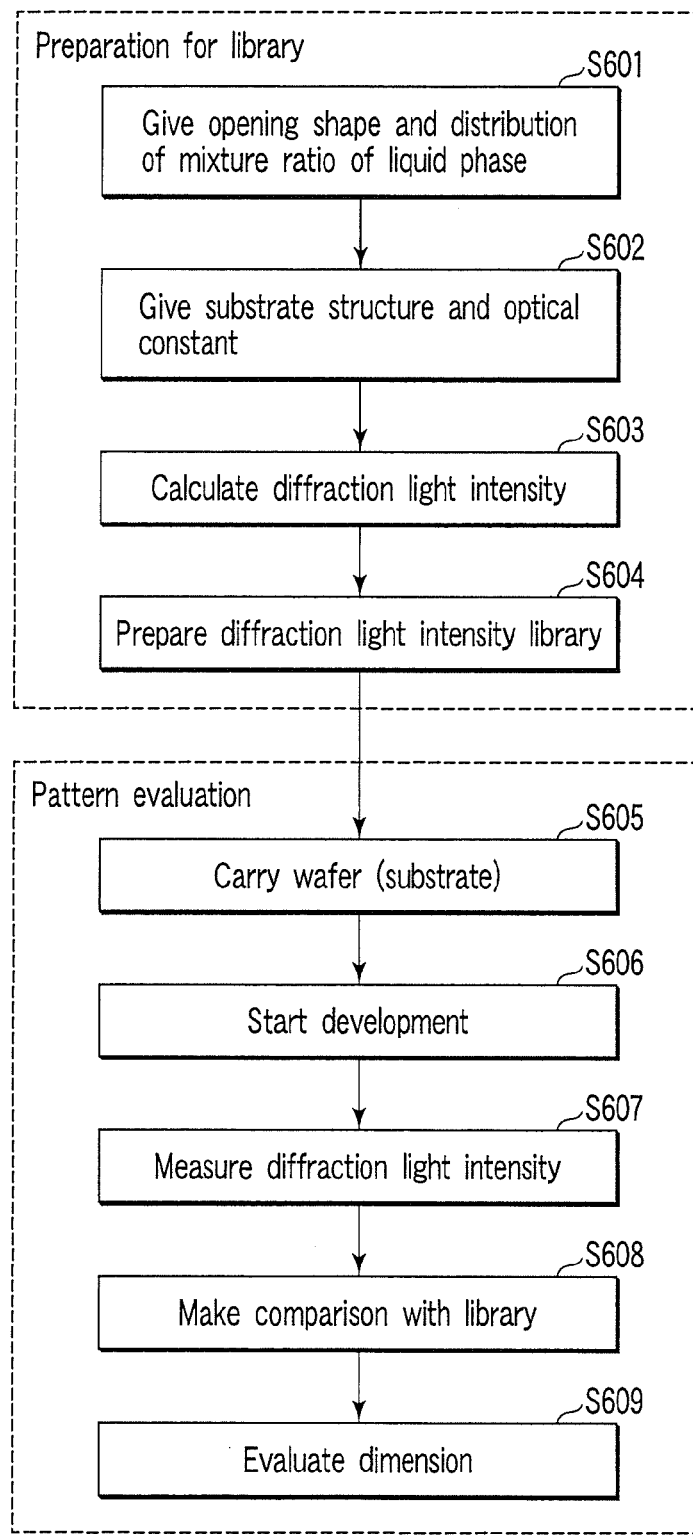
FIG. 21 is a flowchart to explain the procedure of a pattern evaluation method according to the third embodiment.

FIG. 20 is a schematic view to explain the pattern evaluation during development, and FIG. 21 is a flowchart to explain the procedure of a pattern evaluation method. The procedure of the pattern evaluation method of the fourth embodiment will be described below with reference to FIG. 20 and FIG. 21.

As shown in FIG. 20, a resist film 304 is coated on a specified front-end substrate (comprising Si substrate 301, lower-layer film 302 and anti-reflection film 303 in order from the bottom). The resist film 304 is baked and exposed, and thereafter, baked again. After a developer is supplied onto the front-end substrate, light is irradiated to the monitor region on the front-end substrate, and then, a diffraction light is detected. Therefore, in addition to the developer 305, a reaction product of the resist film 304 and a mixed phase of the developer exist over the resist film 304 and each pattern thereof. Broad light having several wavelengths (e.g., halogen lamp light) is used as the incident light. TM deflection intensity of zero-order diffraction light is measured within a wavelength range from 400 to 800 nm. The TM deflection is obtained by arranging a deflection plate in the optical path of the zero-order diffraction light. Wavelength dispersion of the intensity of the diffraction light detected here is uniquely determined depending on the structure of measurement region and optical constant. According to the fourth embodiment, the diffraction light from pattern is measured during development, and dimension is evaluated from the measured result.

The evaluation procedure will be explained below with reference to FIG. 21. In the fourth embodiment, the diffraction light intensity is predicted before the development process, and a library is prepared. The evaluation procedure comprises a process of preparing a library before development and a process of evaluating a pattern dimension in the development process.

In the process of preparing a library, the following parameters are given to determine a development model (step S601). One of the parameters is an opening shape of the development region when the resist film is dissolved in the developer. Another one is a distribution of a mixture ratio of reaction product and developer in a liquid phase consisting of the reaction product of resist and the developer.

Then, the following parameters, that is, substrate structure comprising liquid phase and the substrate with films thereon, and optical constant of a developer, the substrate and the reaction product are given (step S602). Calculation when light is introduced at a specified angle is made based on the given structure and optical constant to obtain a wavelength dispersion of diffraction light intensity (step S603). RCWA (Rigorous coupled-wave analysis) by Morham et al. (J. Opt. Soc. Am., Vol. 12, No. 5, May 1995 1077-1086) is used as the calculation method to acquire electric filed, magnetic field and intensity of refraction light from regular pattern using Maxwell equations. Calculation is made with respect to all conditions of the given structure and optical constant to prepare a wavelength dispersion library of the diffraction light intensity (step S604). The preparation for the library will be described later.

The process of evaluating a pattern dimension will be described below. The substrate (wafer) is carried to a development unit (step S605). A developer is supplied onto the substrate, and then, development is started (step S606). Thereafter, the reflection light of the monitor region is measured (step S607). The position of the substrate and a monitor unit must be controlled so that light advances onto the monitor region and a detector detects the diffraction light. The control may be carried out before the developer is supplied if the substrate is not moved. If not so, the control is carried out after the developer is supplied. A comparison is made between wavelength dispersion of the measured diffraction light intensity and wavelength dispersion of diffraction light stored in the library (step S608). The best wavelength dispersion matching with the wavelength dispersion of diffraction light stored in the library is determined, and thus, pattern dimension is calculated (step S609).

[4-2] Method of Preparing Library

The process of preparing the library will be described below. As described in FIG. 20, the reaction product of resist is generated from the developing resist pattern. In the following description, a developer containing the reaction product of resist call is called a mixed phase, and a ratio of resist in the mixed phase is defined as a mixture ratio. In general, the diffusion velocity of the reaction product is not so fast. For this reason, if the diffusion of the reaction product, that is, a distribution of the mixture ratio in liquid phase is not considered in a model, the accuracy of developing pattern evaluation worsens. In order to solve the problem, a development model considering the distribution is determined in a library preparation process in the fourth embodiment (step S601).

FIG. 22A is a schematic view showing the development progress at the initial development. In the initial development, development advances to the film thickness direction in the development region. As a result, the reaction product diffuses to the direction shown by an arrow (downwardly toward the Si substrate 301). Thus, the mixture ratio has a distribution in a film thickness direction, and the ratio decreases as the position gets away from the Si substrate 301.

When the development in the film thickness direction completes, development advances laterally as illustrated in FIG. 22B. Thus, the reaction product diffuses to direction shown by arrows in FIG. 23 (toward remaining resist film 304 from the opening position of the resist film 304). As a result, the mixture ratio decreases as the position gets away from pattern sidewall in the lateral direction. In fact, the changes of the mixture ratios are overlapped, and thereby, the combined changes make a distribution. According to the distribution, the mixture ratio decreases toward the arrow direction shown in FIG. 23 (i.e., direction separating from the Si substrate 301 and direction toward the opening position from the remaining resist film 304).

Figure 23:
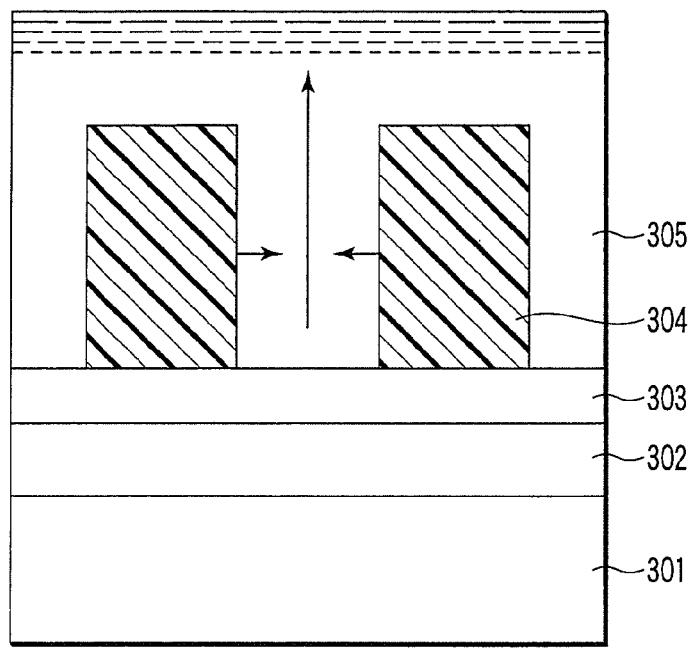
FIG. 23 is a view to explain the diffusion direction of developing reaction products
Figure 24:
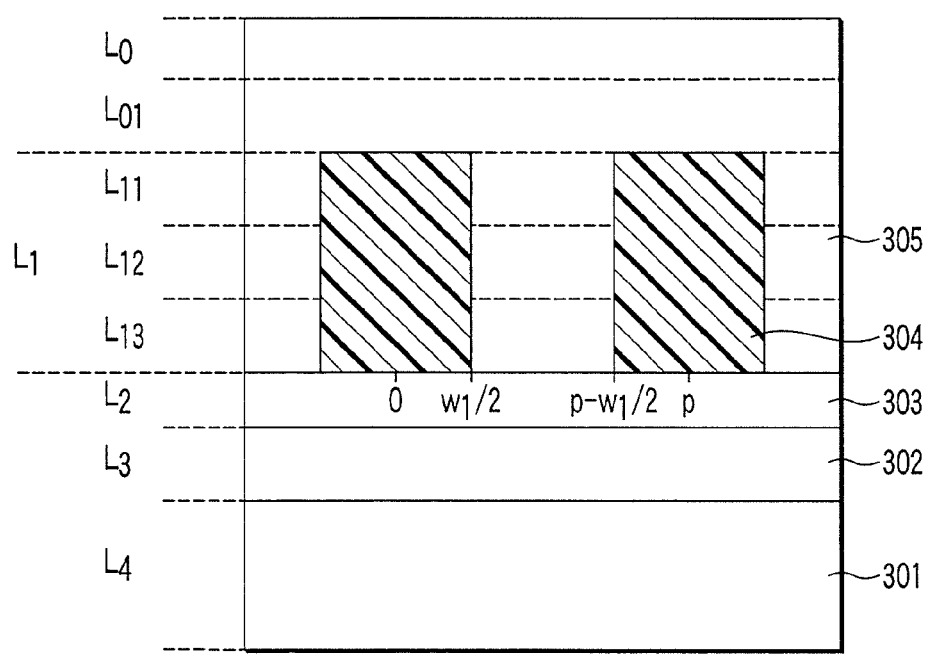
FIG. 24 is a cross-sectional view showing the layer structure along the film thickness direction prepared based on a model shown in FIG. 23.

The following is a description of the step of giving substrate structure and optical constant. FIG. 24 shows a layer structure in the film thickness direction prepared based on the model of FIG. 23. In FIG. 24, p denotes a pattern pitch, and $w_1$ denotes a resist pattern dimension. A layer $L_0$ comprises a developer, and a layer $L_{01}$ comprises the developer and the mixed phase of the reaction product of resist. Layers $L_{11}$ to $L_{13}$ each comprise the developer, the mixed phase of the reaction product of resist and resist pattern. A layer $L_2$ comprises an anti-reflection film. A layer $L_3$ comprises a lower-layer film, and a layer $L_4$ comprises a Si substrate. Layers $L_{11}$ to $L_{13}$ differ from each other in the mixture ratio of the reaction product. The reaction product is generated in the interface between resist and developer, and diffuses to the developer layer; for this reason, the ratio is higher in the lower layer ($L_{13}$) of the pattern.

FIG. 25 shows a distribution of the mixture ratio of Layers $L_0$ to $L_{13}$. The layer $L_0$ comprises only the developer; therefore, the mixture ratio is 0. The layer $L_{01}$ comprises the developer and the mixed phase of the reaction product, and the mixture ratio is set as a fixed value $r_{01}$. Layers $L_{11}$ to $L_{13}$ each comprise the developer, the mixed phase of the reaction product of resist and resist pattern; therefore, the mixture ratio r is given as a positional function, and distributes as shown in FIG. 25. As depicted in FIG. 25, the mixture ratio is 0 in the resist pattern region ($0<x<w_1/2$, $p-w_1/2<x<p$). The mixture ratio takes a value between 0 and 1 in a mixed phase region of the developer and the reaction product of resist ($w_1/2$, $<x<p-w_1/2$). Layers $L_{11}$, $L_{12}$ and $L_{13}$ each take a function corresponding to the position, that is, $r_{11}(x)$, $r_{12}(x)$ and $r_{13}(x)$. The functions $r_{11}(x)$ to $r_{13}(x)$ have a relation such that the mixture ratio decreases as the position gets away from the interface between liquid phase and substrate.

Based on the distribution of the mixture ratio shown in FIG. 25, parameters required for obtaining structure and optical constant are given. The parameters include each refractive index, extinction coefficient, film thickness and dimension of layers $L_0$ to $L_4$. Table 10 shows given refractive index, extinction coefficient, film thickness and dimension of the layers $L_0$ to $L_4$. FIG. 26 shows a refractive index of each layer. FIG. 27 shows an extinction coefficient of each layer. The refractive index and the extinction coefficient of layers $L_{01}$, $L_{11}$ to $L_{13}$ are expressed as a function of the position (x).

TABLE 10

| Layer | Refractive index | Extinction coefficient | Film thickness | Dimension |
|---|---|---|---|---|
| $L_0$ | $n_0$ | $k_0$ | — | — |
| $L_{01}$ | $n_{01}$ | $k_{01}$ | $d_{01}$ | — |
| $L_{11}$ | $n_{11}(x)$ | $k_{11}(x)$ | $d_{11}$ | $w_1$ |
| $L_{12}$ | $n_{12}(x)$ | $k_{12}(x)$ | $d_{12}$ | |
| $L_{13}$ | $n_{13}(x)$ | $k_{13}(x)$ | $d_{13}$ | |
| $L_2$ | $n_2$ | $k_2$ | $d_2$ | — |
| $L_3$ | $n_3$ | $k_3$ | $d_3$ | — |
| $L_4$ | $n_4$ | $k_4$ | — | — |

The layer $L_0$ comprises the developer only; therefore, the refractive index no and the extinction coefficient $k_0$ both take the value of the developer. The layer $L_{01}$ comprises the developer and the mixed phase of the reaction product of resist; therefore, the refractive index $n_{01}$ and the extinction coefficient $k_{01}$ both take a value between that of the developer ($n_0$, $k_0$) and the resist ($n_1$, $k_1$). The film thickness is $d_{01}$.

Layers $L_{11}$ to $L_{13}$ each comprise the developer and the mixed phase of the reaction product of resist and resist pattern. Therefore, the refractive index and the extinction coefficient are expressed as a function of the position, and given as shown in FIG. 26 and FIG. 27, respectively. In the resist pattern region ($0<x<w_1/2$, $p-w_1/2<x<p$), the refractive index and the extinction coefficient both take the resist value ($n_1$, $k_1$). In the mixed phase region of the developer and the reaction product of resist ($w_1/2<x<p-w_1/2$), the refractive index and the extinction coefficient both take a value between that of the developer and the reaction product. These film thicknesses are respectively $d_{11}$, $d_{12}$ and $d_{13}$.

The layer $L_2$ comprises an anti-reflection film; therefore, the refractive index $n_2$ and the extinction coefficient $k_2$ both take a value of the anti-reflection film. The film thickness is $d_2$. The layer $L_3$ comprises a lower-layer film; therefore, the refractive index $n_3$ and the extinction coefficient $k_3$ both take a value of the lower-layer film. The film thickness is $d_3$. The layer $L_4$ comprises a Si substrate; therefore, the refractive index $n_4$ and the extinction coefficient $k_4$ both take a value of the Si substrate.

It is assumed that parameters variable in the process are film thickness $d_1$, refractive index $n_{01}$, and extinction coefficient $k_{01}$ of layer $L_{01}$, film thickness $d_{11}$, refractive index $n_{11}$ (x), and extinction coefficient $k_{11}$ (x) of layer $L_{11}$, film thickness $d_{12}$, refractive index $n_{12}$, and extinction coefficient $k_{12}$ (x) of layer $L_{12}$ film thickness $d_{13}$, refractive index $n_{13}$ (x), and extinction coefficient $k_{13}$ of layer $L_{13}$, dimension $w_1$ of layer $L_1$, film thickness $d_2$ of layer $L_2$, and film thickness $d_3$ of layer $L_3$. Then, if each parameter has five levels, the combination of structures and optical constants are given as $5^9$, that is, 1953125 (step S601, S602). The refractive index and the extinction coefficient change depending on the diffusion of the reaction product. Calculation is made with respect to each structure and optical constant (step S603), and 1953125 wavelength dispersions of diffraction light intensity are prepared (step S604).

In a comparison of measured waveform in pattern evaluation (step S608), wavelength dispersion of measured reflection light intensity is compared with wavelength dispersion of measured reflection light intensity stored in the library to calculate a dimension.

[4-3] Advantages

Figure 28:
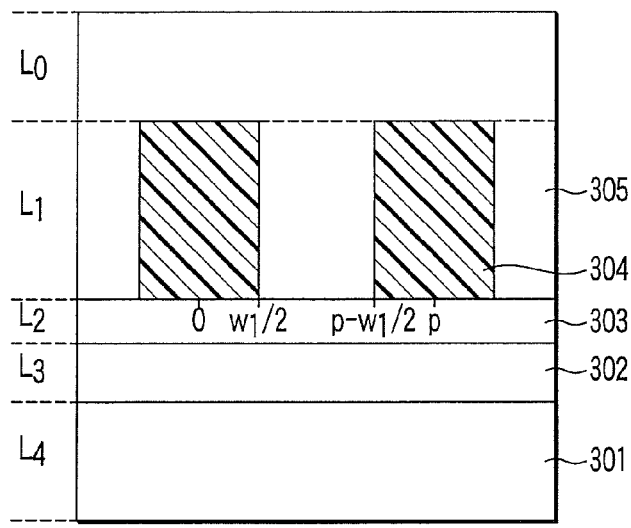
FIG. 28 is a view showing a conventional development model.
Figure 29:
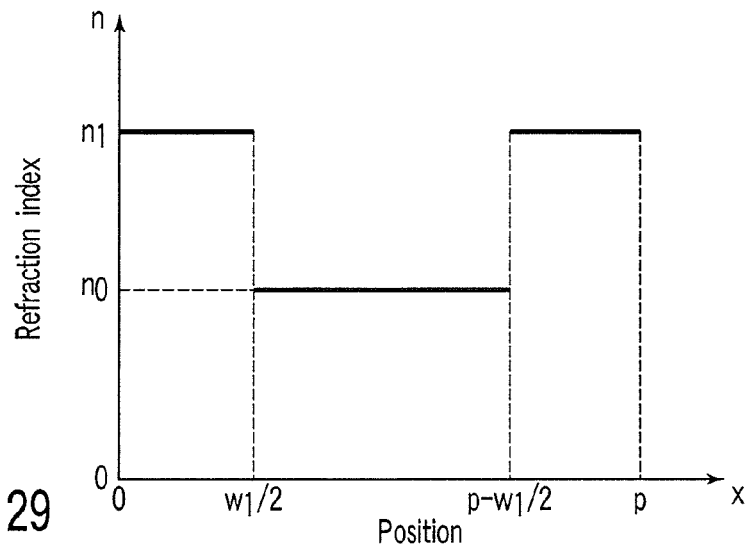
FIG. 29 is a chart showing the distribution of an refractive index based on a conventional model.
Figure 30:
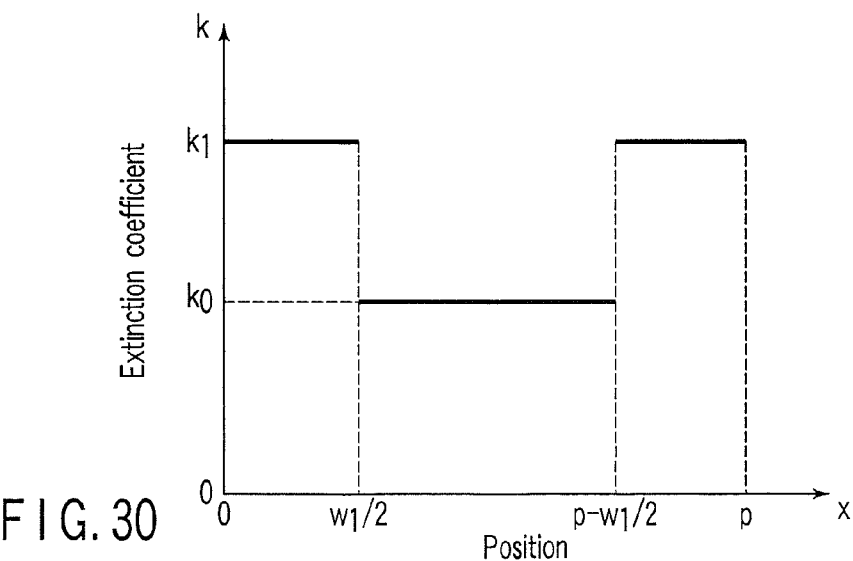
FIG. 30 is a chart showing the distribution of an extinction coefficient based on a conventional model.

For comparison, a conventional developer model is shown in FIG. 28. As seen from FIG. 28, no consideration is taken with respect to the distribution of the mixture ratio of the developer and the reaction product in the film thickness direction. In addition, no consideration is taken with respect to the distribution of the mixture ratio of the developer and the reaction product between resist patterns. The following Table 11 shows values of refractive index, extinction coefficient, film thickness and dimension. The refractive index and extinction coefficient of the conventional developer model are shown in FIG. 29 and FIG. 30, respectively.

TABLE 11

| Layer | Refractive index | Extinction coefficient | Film thickness | Dimension |
|---|---|---|---|---|
| $L_0$ | $n_0$ | $k_1$ | — | — |
| $L_1$ | $n_1(x)$ | $k_1(x)$ | $d_1$ | $w_1$ |
| $L_2$ | $n_2$ | $k_2$ | $d_2$ | |
| $L_3$ | $n_3$ | $k_3$ | $d_3$ | |
| $L_4$ | $n_4$ | $k_4$ | | |

It is assumed that parameters variable in the process are film thickness $d_1$ and dimension $w_1$ of layer $L_{01}$, film thickness $d_2$ of layer $L_2$ and film thickness $d_3$ of layer $L_3$. Then, if each parameter has five levels, structure and optical constant are given as $5^4$ that is, 625. Calculation is made with respect to each structure and optical constant, and 625 wavelength dispersions of diffraction light intensities are prepared. Wavelength dispersion of measured reflection light intensity is compared with 626 wavelength dispersions to calculate a dimension.

The method of the fourth embodiment has the following effect as compared with the conventional method. According to the method of this embodiment, consideration is given to the mixture ratio of the reaction product of resist and the developer. Thus, a great number of samples of wavelength dispersion are stored in the library; therefore, high accuracy is obtained.

The wavelength dispersion is measured in the fourth embodiment. A single wavelength, however, may be measured if sufficient accuracy is obtained using the single wavelength. The library may be prepared during the development process instead of preparing it before the development process. The pattern dimension is evaluated in the fourth embodiment. A pattern shape and the mixture ratio of developer and reaction product, however, may be evaluated.

TM deflection light is evaluated using a deflection plate in the fourth embodiment, however, it may be detected without using the deflection plate if sufficient accuracy is obtained. Evaluation may be carried out with respect to TE deflection light, other deflection lights, intensity change (Tan ψ) and phase change (cos Δ). First-order or more diffraction lights may be detected. The angle of incident light is not necessarily vertical.

1953125 wavelength dispersion samples are subjected to the comparison because the mixture ratio model is complicated in the fourth embodiment. However, if the time zone for carrying out evaluation is the second-half of the development, the reaction product has already considerably diffused at the point. Therefore, a comparison with a library including a model having no diffusion advance of the reaction product is not made, and thereby, the process time is shortened. Therefore, it is effective to determine comparative data in accordance with time zone.

(5) Fifth Embodiment

The fifth embodiment relates a pattern forming method.

The drawing schematically showing pattern during development is FIG. 11A to FIG. 11C like the third embodiment. The drawing shown as the flowchart to explain the procedure is FIG. 31. The procedure of the present invention will be described below with reference to FIG. 11A to FIG. 11C and FIG. 31.

As shown in FIG. 11A to FIG. 11C, a resist film 505 is coated on a specified front-end substrate (comprising Si substrate 501, lower-layer film 502, 503 and anti-reflection film 504 in order from the bottom). The resist film 505 is baked and exposed, and thereafter, baked again. After a developer is supplied onto the front-end substrate, light is irradiated to the monitor region on the front-end substrate, and then, a diffraction light is detected. Broad light having several wavelengths (e.g., halogen lamp light) is used as the incident light. Thus, the intensity of zero-order diffraction light is measured within a wavelength range from 400 to 800 nm without using a deflection plate. Wavelength dispersion of the intensity of the diffraction light detected is uniquely determined depending on the structure of measurement region and optical constant. According to the fifth embodiment, the diffraction light from pattern is measured during development, and dimension is evaluated from the measured result. Further, development ends in accordance with the measured result.

Figure 31:
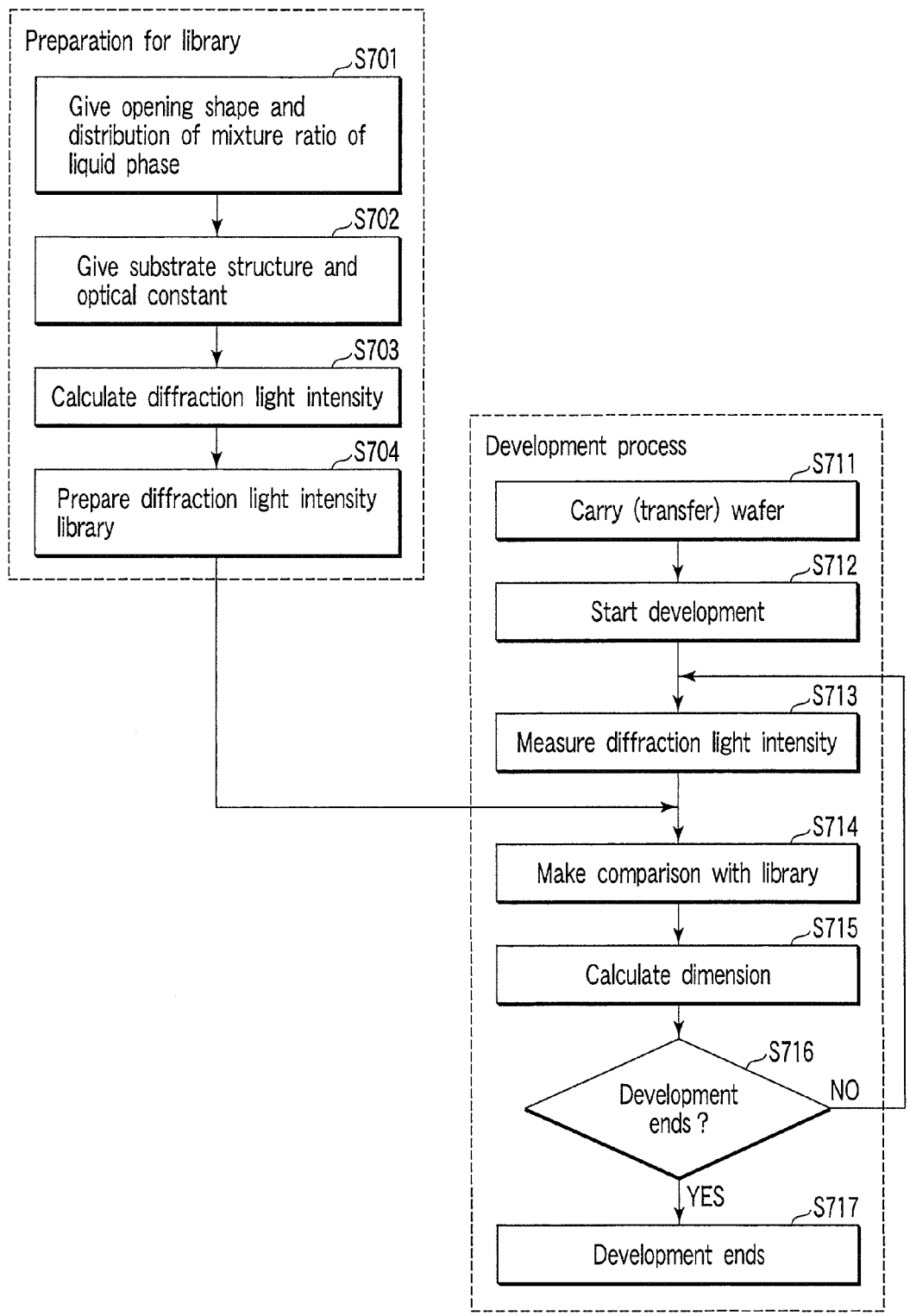
FIG. 31 is a flowchart to explain the procedure of a pattern evaluation method according to a fourth embodiment of the present invention.

The procedure will be explained below with reference to FIG. 31. In the fifth embodiment, the diffraction light intensity is predicted before the development process, and a library is prepared. The evaluation procedure comprises a process of preparing a library before development and a development process. In the process of preparing a library, the following parameters are given to determine a development model (step S701). One of the parameters is an opening shape of the development region when the resist film is dissolved in the developer. Another one is a distribution of a mixture ratio of reaction product and developer in a liquid phase consisting of the reaction product of resist and the developer.

Then, the following parameters, that is, substrate structure comprising liquid phase and the substrate with films thereon, and optical constant are given (step S702).

Calculation when light is introduced at a specified angle is made based on the given structure and optical constant to calculate a wavelength dispersion of diffraction light intensity (step S703).

Calculation is carried out with respect to all conditions of the given structure and optical constant to prepare a wavelength dispersion library of diffraction light intensity (step S704). RCWA (Rigorous coupled-wave analysis) by Morham et al. (J. Opt. Soc. Am., Vol. 12, No. 5, May 1995 1077-1086) is used as the calculation method to acquire electric filed, magnetic field and intensity of refraction light from regular pattern using Maxwell equations. Calculation is made with respect to all conditions of the given structure and optical constant.

The development process will be described below. The substrate (wafer) is carried to a development unit (step S711). Developer is supplied onto the substrate, and then, development is started (step S712). Thereafter, the reflection light of the monitor region is measured (step S713). The position of the substrate and the monitor unit must be controlled so that light advances onto the monitor region and a detector detects diffraction light. The control may be carried out before the developer is supplied if the substrate is not moved. If not so, the control is carried out after the developer is supplied. A comparison is made between wavelength dispersion of the measured diffraction light intensity and wavelength dispersion of diffraction light stored in the library. The best wavelength dispersion matching with the wavelength dispersion of diffraction light stored in the library is determined (step S714), and thus, pattern dimension is calculated (step S715).

The calculated dimension is compared with a desired dimension to determine if the development should end or not. If the calculated dimension matches the desired value, the development is finished (step S717). If not, the reflection light is again measured (step S713), and then, a comparison with the wavelength dispersion library is made (step S714). The foregoing procedure is continuously taken until the calculated pattern dimension reaches the desired value.

The fifth embodiment differs from the third embodiment in way of giving structure and optical constant (step S702). The difference will now be explained. The development model and the schematic view of film structure are the same as the third embodiment and are shown in FIG. 23 and FIG. 24, respectively. The distribution of optical constants of the layer L1 is the same as the first embodiment and is shown in FIG. 26 and FIG. 27. According to the fifth embodiment, structure and optical constant are given (the same as the third embodiment so far), and thereafter, average of the optical constant is made in each layer. The optical constant of each layer is given as a fixed value. Therefore, a refractive index $n_{1i}$ of a layer $L_{1i}$ is obtained from the following equation.

$$n_{1i} = \frac{1}{p}\int_0^p n_{1i}(x)dx$$

An extinction coefficient $k_{1i}$ of the layer $L_{1i}$ is obtained from the following equation.

$$k_{1i} = \frac{1}{p}\int_0^p k_{1i}(x)dx$$

Consequently, finally obtained structure and optical constant are as shown in the following Table.

TABLE 12

| Layer | Refractive index | Extinction coefficient | Film thickness | Dimension |
|---|---|---|---|---|
| $L_0$ | $n_0$ | $k_0$ | — | — |
| $L_{01}$ | $n_{01}$ | $k_{01}$ | $d_{01}$ | — |
| $L_{11}$ | $n_{11}(x)$ | $k_{11}(x)$ | $d_{11}$ | $w_1$ |
| $L_{12}$ | $n_{12}(x)$ | $k_{12}(x)$ | $d_{12}$ | |
| $L_{13}$ | $n_{13}(x)$ | $k_{13}(x)$ | $d_{13}$ | |
| $L_2$ | $n_2$ | $k_2$ | $d_2$ | — |
| $L_3$ | $n_3$ | $k_3$ | $d_3$ | — |
| $L_4$ | $n_4$ | $k_4$ | — | — |

It is assumed that parameters variable in the process are film thickness $d_{01}$ of layer $L_{01}$, the way of diffusion of reaction product $(n_{01}, k_{01})$ in the layer $L_{01}$, film thickness $(d_{11})$ of layer $L_{11}$, the way of diffusion of reaction product $(n_{11}, k_{11})$ in the layer $L_{11}$, film thickness $(d_{12})$ of layer $L_{12}$, the way of diffusion of reaction product $(n_{12}, k_{12})$ in the layer $L_{12}$, film thickness $(d_{13})$ of layer $L_{13}$, the way of diffusion of reaction product $(n_{13}, k_{13})$ in the layer $L_{13}$, dimension $w_1$ of layer $L_1$, film thickness $(d_2)$ of layer $L_2$, and film thickness $(d_3)$ of layer $L_3$. If each parameter has five levels, the combination of structures and optical constants are given as $5^9$, that is, 1953125 (step S701, S702). Calculation is carried out with respect to each combination (step S703), and thus, 1953125 wavelength dispersions of diffraction light intensity are prepared (step S704).

In a comparison of measured wavelength in pattern evaluation (step S714), the wavelength dispersion of the measured reflection light intensity is compared with those stored in the library to calculate a dimension, and thereafter, development ends. High accuracy is obtained by using the library considering the mixture ratio of the reaction product of resist and the developer rather than using the library giving no consideration described above.

The wavelength dispersion is measured in the fifth embodiment, however a single wavelength may be measured if sufficient accuracy is obtained using the single wavelength. The library is prepared before the development process in the fifth embodiment, however it may be prepared during the development process.

In the fifth embodiment, evaluation is made without using the deflection plate, however evaluation may be carried out with respect to TE deflection light, other deflection lights, intensity change (Tan ψ) and phase change (cos Δ). First-order or more diffraction lights may be detected. The angle of incident light is not necessarily vertical.

In the fifth embodiment, the library stores 1953125 wavelength dispersion samples because the mixture ratio model is complicated. However, the reaction product has already considerably diffused in the second-half of the development and the comparison with samples including small advance of diffusion may be omitted, thereby shortening the comparison time. On the other hand, the reaction product has not diffused so much in the first-half of the development. Therefore, the comparison with samples including big advance of diffusion may be omitted to shorten the comparison time. Consequently, it is effective to determine data to be compared in accordance with time zone.

According to the fifth embodiment, the development model of the liquid phase comprising the reaction product of resist and the developer is clarified. In other words, it is assumed that the resist ratio in the mixed phase simply changes to 0 as the position in the mixed phase gets away from the interface between the mixed phase and the resist. This assumption is used, and thereby, it is possible to accurately predict the diffraction light intensity of developing pattern. As a result, the evaluation accuracy of patterns is greatly improved.

(6) Sixth Embodiment

The sixth embodiment relates to a resist pattern process condition determination system.

FIG. 32 is a view showing the configuration of a resist pattern process condition determination system according to a fifth embodiment of the present invention.

The system is composed of coater/developer equipment, transport equipment 408 and exposure equipment 406. The coater/developer equipment comprises comparison operation feedback section 401, coating unit 402 using spin coating, post-coating baking unit 403, post-exposure baking (PEB) unit 404 and development unit 405. The development unit 405 includes a shape measuring instrument 405a. The transport equipment 408 can carry a wafer between the exposure equipment 406 and a carrier station 407 and between the foregoing units at 1 wafer unit. The coating unit 402 may be equipped with a chemical solution control section 402a. The chemical solution control section 402a mixes first resist solution (not shown) and second resist solution (solvent or photosensitive solution, solution partially extracted from the first resist solution). The control section supplies the mixed chemical solution to a nozzle for dropping chemical solution on a substrate.

The comparison operation feedback section 401 has experiment plane registration section 401a, margin registration section 401b and control value predicting section 401c.

The following is a description of the method of determining the optimum process condition of a resist newly developed using the foregoing system. The method will be explained below using part of experiment results. The carrier station 407 of the system was loaded with 24 substrates (wafers). The loaded substrates are processed at a unit of several substrates.

Figure 33:
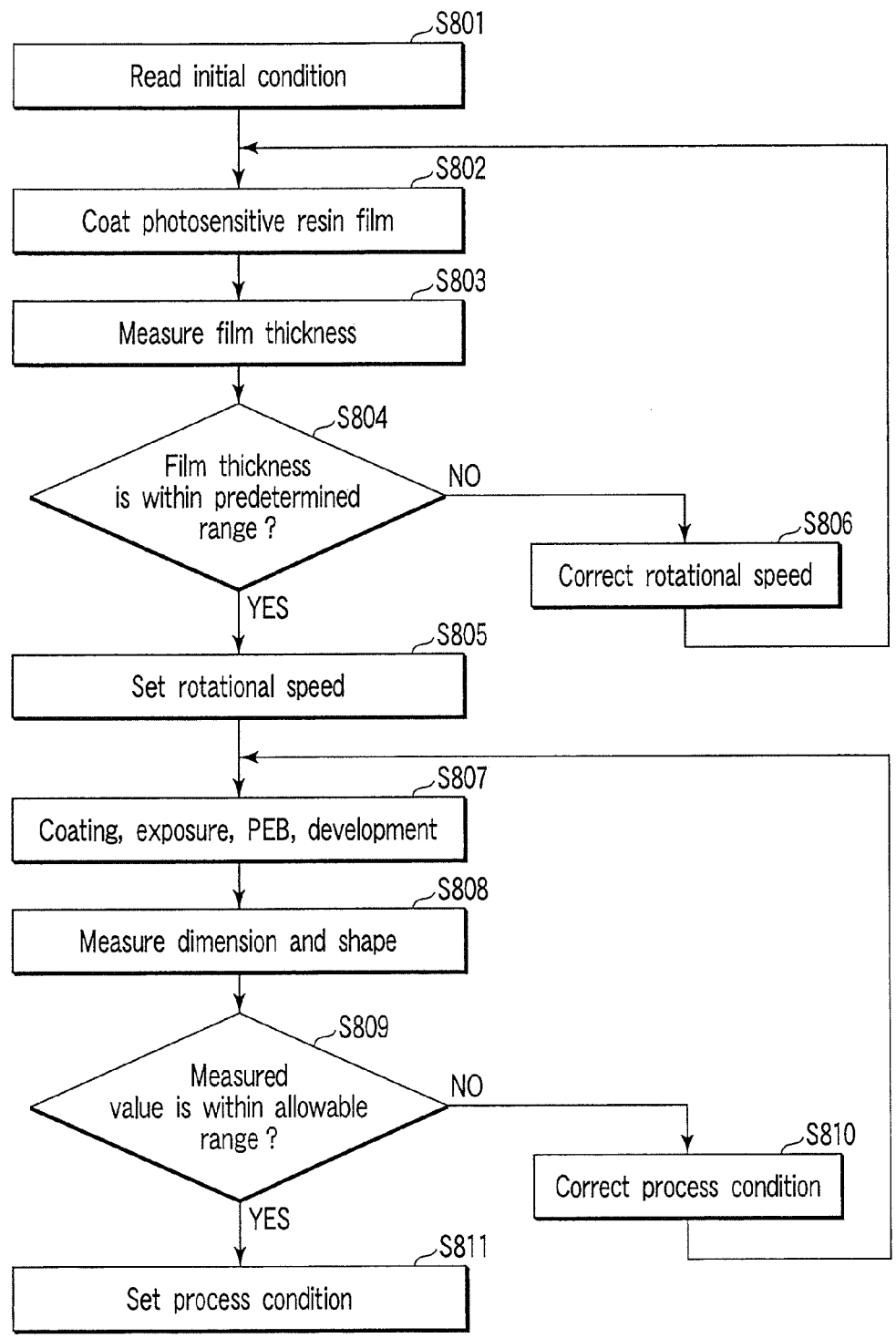
FIG. 33 is a flowchart to explain the procedure of a process condition determination method according to a fifth embodiment of the present invention.

The procedure of automatically determining the process condition will be described below with reference to FIG. 33. FIG. 33 is a flowchart to explain the procedure of a process condition determination method according to a fifth embodiment of the present invention.

The initial condition recorded in the coater/developer equipment and the exposure equipment 406 is read (step S801). In the coating unit 402, a coating film is formed with respect to three substrates according to a rotational speed of the initial condition shown in the following Table 13 (step S802).

TABLE 13

|  |  | 1 | 2 | 3 |
|---|---|---|---|---|
| Coating | Number of revolutions (rpm) | 2000 | 2500 | 3000 |
|  | Supply Amount of solution (cc) | 2 | ← | ← |

The shape measuring instrument 405a measures the film thickness of a photosensitive resin film immediately after coating (step S803). The comparison operation feedback section 401 compares the measured film thickness with a predetermined range (step S804).

If the film thickness is within the predetermined range, the rotational speed of the initial condition is set as the process condition (step S805). If the film thickness is not within the predetermined range, the comparison operation feedback section 401 determines the optimum rotational speed required for obtaining a desired film thickness based on the relationship between rotational speed and film thickness (step S806). In the sixth embodiment, a resist film having the predetermined range was not obtained under the condition shown in the Table 13. Then, the rotational speed was corrected as 2400 rpm; as a result, a resist film having a predetermined range was obtained. Thus, the 2400 rpm was set as the process condition.

Then, the following plan was made. More specifically, exposure and focus position are each changed on the surface of the substrate. Three parameters, that is, the temperature and time of post-exposure bake (PEB) for each substrate and development time are given, and each of these parameters has two levels. The experiment plan is stored in the experiment plan registration section 401a. Based on the experiment plan, coating, exposure, post-exposure bake (PEB), development and shape measurement are successively carried out to the total of eight substrates (step S807). The following Table 14 shows setting values of each parameter.

TABLE 14

|  |  | 4 | 5 | 6 | 7 | 8 | 9 | 10 | 11 |
|---|---|---|---|---|---|---|---|---|---|
| Coating | Number of revolutions (rpm) | 2400 | ← | ← | ← | ← | ← | ← | ← |
|  | Supply amount (cc) | 2 | ← | ← | ← | ← | ← | ← | ← |
| PEB | Temperature (° C.) | 130 | 140 | 130 | 130 | 140 | 140 | 130 | 140 |
|  | Time (second) | 60 | 60 | 60 | 90 | 90 | 60 | 90 | 90 |
| Development | Concentration N | 0.27 | ← | ← | ← | ← | ← | ← | ← |
|  | Temperature (° C.) | 25 | ← | ← | ← | ← | ← | ← | ← |
|  | Time (second) | 30 | 60 | 60 | 30 | 60 | 30 | 60 | 30 |

The shape measuring instrument 405a measures the dimension and shape of an opening portion (region without photosensitive resin) of photosensitive resin pattern (step S808). The dimension and shape are measured using RCWA by Morham et al. (J. Opt. Soc. Am., Vol. 12, No. 5, May 1995 1077-1086) is used as the calculation method to obtain electric filed, magnetic field and intensity of refraction light from regular pattern using Maxwell equations.

It is determined whether or not the measured value is within an allowable range (step S809). The allowable range of the pattern dimension is 100 nm±5%. The allowable range of the pattern shape is a range from 88° to 90° at a sidewall angle.

If the measured value is within the allowable range, another exposure-focus range (ED-margin) to obtain a shape within the range to determine wider ED-margin as much as possible. The ED-margin is registered in the margin registration section 401b.

ED-margin data about eight substrates was compared with the level of coating, PEB and development. This comparison shows that longer bake time realizes the wider ED-margin. Therefore, the comparison operation feedback section 401 allocates longer time of the two levels to the post-exposure baking unit 404. The control value predicting section 401c of the comparison operation feedback section 401 takes the setting procedure given below. More specifically, the control value predicting section 401c determines that interaction exists between bake temperature and development time. The section 401c sets the bake temperature to an optimum temperature and ±2° C. (smaller than the temperature range used for the first-time experiment level) thereof (three levels). Likewise, section 401c sets the development time to an optimum time and ±10% (smaller than the time range used for the first-time experiment level) thereof (three levels). As a result, the comparison operation feedback section 401 gave instructions to coating unit 402, post-exposure bake (PEB) unit 404, development unit 405 and exposure equipment 406 to carry out coating, exposure, PEB, development and shape measurement on the total of nine substrates.

As described above, the photosensitive resin pattern forming system automatically measures the dimension and shape of the photosensitive resin pattern in the process of treating the total of 20 substrates and feeds the result back to associated means to determine coating, bake, exposure and development conditions.

A semiconductor device with largely improved dimension accuracy was realized when the semiconductor device is obtained through carrying out etching with a photosensitive resin pattern as a mask which is formed in accordance with the conditions determined in the manner. This semiconductor device has a greatly high reliability.

It took two minutes to determine the film thickness and to make feedback, and 23 minutes to make evaluation of 3 parameters having two levels, and 25 minutes to determine detailed conditions (2 parameters having 3 levels) in the operation. Thus, patterning using a new photosensitive resin material is optimized in about 50 minutes. On the other hand, the conventional destructive inspection needed eight days. Therefore, the present embodiment can greatly reduce condition determination time.

The number of substrates required for determining selected parameters, level, correction target and conditions is not limited to the foregoing embodiment. In this case, various procedures may be taken in accordance with target photosensitive resin material, required items and values to photosensitive resin pattern and its range.

Incidentally, fine control for the level is preferably carried out in the following manner.

1) Correction on resist pattern dimension of positive resist a) If dimension is thicker than desired one, any of corrections given below is made.

The corrections include:

increasing the exposure of exposure means;

increasing the bake temperature of bake means used for post-exposure bake;

lengthening the development time of development means;

increasing the developer concentration of development means; and increasing the developer temperature of development means

TABLE 15

| | | 12 | 13 | 14 | 15 | 16 | 17 | 18 | 19 | 20 |
|---|---|---|---|---|---|---|---|---|---|---|
| Coating | Number of revolutions (rpm) | 2400 | ← | ← | ← | ← | ← | ← | ← | ← |
| | Supply amount (cc) | 2 | ← | ← | ← | ← | ← | ← | ← | ← |
| PEB | Temperature (° C.) | 135 | 133 | 137 | 137 | 135 | 135 | 133 | 133 | 137 |
| | Time (second) | 60 | ← | ← | ← | ← | ← | ← | ← | ← |
| Development | Concentration N | 0.27 | ← | ← | ← | ← | ← | ← | ← | ← |
| | Temperature (° C.) | 25 | ← | ← | ← | ← | ← | ← | ← | ← |
| | Time (second) | 40 | 36 | 36 | 44 | 44 | 36 | 44 | 40 | 40 |

The comparison operation feedback section 401 finds a condition that can realize the maximum ED-margin, and determines the optimum condition corresponding to the condition was +0.4° C. to the standard for bake temperature and −5% of the standard for development time. Then, the comparison operation feedback section 401 sets the optimum condition to baking unit and development unit. In addition, the section 401 sets focus offset and optimum exposure to the exposure equipment.

b) If dimension is thinner than desired one, any of corrections given below is made.

The corrections include:

decreasing the exposure of exposure means;

decreasing the bake temperature of bake means used for post-exposure bake;

shortening the development time of development means;

decreasing the developer concentration of development means; and decreasing the developer temperature of development means 2) Correction on opening dimension of positive resist
a) If dimension is thicker than desired one, any of corrections given below is made.
The corrections include:
decreasing the exposure of exposure means;
decreasing the bake temperature of bake means used for post-exposure bake;
shortening the development time of development means;
decreasing the developer concentration of development means; and
decreasing the developer temperature of development means
b) If dimension is thinner than desired dimension, any of corrections given below is made.
The corrections include:
increasing the exposure of exposure means;
increasing the bake temperature of bake means used for post-exposure bake;
lengthening the development time of development means;
increasing the developer concentration of development means; and
increasing the developer temperature of development means 3) Correction on resist pattern dimension of negative resist
a) If dimension is thicker than desired dimension, any of corrections given below is made.
The corrections include:
decreasing the exposure of exposure means;
decreasing the bake temperature of bake means used for post-exposure bake;
shortening the development time of development means;
decreasing the developer concentration of development means; and
decreasing the developer temperature of development means
b) If dimension is thinner than desired dimension, any of corrections given below is made.
The corrections include:
increasing the exposure of exposure means;
increasing the bake temperature of bake means used for post-exposure bake;
lengthening the development time of development means;
increasing the developer concentration of development means; and
increasing the developer temperature of development means 4) Correction on opening dimension of negative resist
a) If dimension is thicker than desired dimension, any of corrections given below is made.
The corrections include:
increasing the exposure of exposure means;
increasing the bake temperature of bake means used for post-exposure bake;
lengthening the development time of development means;
increasing the developer concentration of development means; and
increasing the developer temperature of development means
b) If dimension is thinner than desired dimension, any of corrections given below is made.
The corrections include:
decreasing the exposure of exposure means;
decreasing the bake temperature of bake means used for post-exposure bake;
shortening the development time of development means;
decreasing the developer concentration of development means; and
decreasing the developer temperature of development means RCWA is employed for shape measurement in the sixth embodiment, however any other methods are applicable to shape measurement means so long as they predict pattern dimension and shape.

The sixth embodiment relates to condition determination for forming resist pattern in the lithography process, however it is not limited to the process. The present embodiment is applicable to condition determination in the etching process. If a process condition determination apparatus includes resist control means, resist solution may be simultaneously optimized. According to the sixth embodiment, chemical solution is prepared for each kind of resin, photosensitive agent, anti-soluble material and solvent in the resist control means. The chemical solution having a blend ratio changed using a mixer is coated on the substrate. By doing so, conditions such as coating, bake and development are optimized while materials are optimized. Therefore, material maker carries out the foregoing embodiments of the present invention, and thereby, it is possible to readily sell materials attached with optimum process condition.

In each of embodiments of the present invention, samples with respect to all combinations of setting level are prepared as the experiment plan; however, the present invention is not limited to above. Taguchi method using orthogonal table such as L18 may be employed, and thereby, the possibility of finding optimum condition using reduced samples is high.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A structure inspection method comprising:
preparing a substrate having layers whose structure is characterized by an optical constant, film thickness, ratio and pitch, the substrate having one or more structure-determined layer and one or more structure-undetermined layer;
preparing predicted structures of each of the layers;
preparing a substrate structure library storing substrate structures comprising combinations of the structures in each of the layers;
making light enter each of the substrate structures at a specified angle and calculating a light intensity of the light which is diffracted or reflected from the substrate structure, thereby preparing a first light intensity library storing the substrate structures and the light intensity calculated to each of the substrate structures;
newly preparing structures including a structure of a structure-determined layer;
extracting a substrate structure including one of the newly prepared structures from the substrate structures in the first light intensity library, and preparing a second light intensity library storing the extracted substrate structure and a light intensity calculated with respect to the extracted substrate structure;
making light enter the substrate at the specified angle and detecting a light intensity of light which is diffracted or reflected from the substrate; and comparing the detected light intensity with the light intensity stored in the second light intensity library to determine a structure of the substrate.

2. The method according to claim 1, wherein said preparing predicted structures of each of the layers includes:
preparing a structure included in a range which is defined by two times as much as a predicted fluctuation value from a target value of the structure of the layer during a process of forming the layer with the target value used as a center.

3. The method according to claim 1, wherein said newly preparing structures including a structure of a structure-determined layer includes
preparing a structure included in a range which is defined by two times as much as an inspection difference with the structure of the structure-determined layer used as a center.

4. The method according to claim 1, wherein the specified angle includes a plurality of angles.

5. The method according to claim 1, wherein the light includes a plurality of wavelengths.

6. The method according to claim 1, wherein the light intensity is calculated using RCWA (Rigorous coupled-wave analysis) method.

7. A structure inspection method comprising:
preparing a substrate having layers whose structure is characterized by an optical constant, film thickness, ratio and pitch, the substrate having one or more structure-determined layer and one or more structure-undetermined layer;
preparing predicted structures of each of the layers;
preparing a substrate structure library storing substrate structures comprising combinations of the structures in each of the layers;
newly preparing structures of the structure-determined layers based on a structure of the structure-determined layer;
extracting a substrate structure including the newly prepared structures from the first substrate structure library, preparing a second substrate structure library;
predicting a light intensity of light which is diffracted or reflected from the substrate structure by calculation when making light enter each of the substrate structures in the second substrate structure library at a specified angle;
making light enter the substrate at the specified angle and detecting a light intensity of light which is diffracted or reflected from the substrate; and
comparing the detected light intensity with the predicted light intensity, thereby determining a structure of the substrate.

8. The method according to claim 7, wherein said preparing predicted structures of each of the layers includes:
preparing a structure included in a range which is defined by two times as much as a predicted fluctuation value from a target value of the structure of the layer during a process of forming the layer with the target value used as a center.

9. The method according to claim 7, wherein said newly preparing structures including a structure of a structure-determined layer includes
preparing a structure included in a range which is defined by two times as much as an inspection difference with the structure of the structure-determined layer used as a center.

10. The method according to claim 7, wherein the specified angle includes a plurality of angles.

11. The method according to claim 7, wherein the light includes a plurality of wavelengths.

12. The method according to claim 7, wherein the light intensity is calculated using RCWA (Rigorous coupled-wave analysis) method.

13. A structure inspection method comprising:
preparing a substrate having layers whose structure is characterized by an optical constant, film thickness, ratio and pitch, the substrate having one or more structure-determined layer and one or more structure-undetermined layer;
preparing predicted structures of each of the structure-undetermined layers;
preparing determined structure including a structure of the structure-determined layer;
preparing a substrate structure library storing substrate structures comprising combinations of the predicted structures and the determined structure;
making light enter at a specified angle the substrate structures stored in the substrate structure library and predicting a light intensity of light which is diffracted or reflected from the substrate structure by calculation;
making light enter the substrate at the specified angle and detecting a light intensity of light which is diffracted or reflected from the substrate; and
comparing the detected light intensity with the predicted light intensity, thereby determining a structure of the substrate.

14. The method according to claim 13, wherein said preparing predicted structures of each of the structure-undetermined layers includes:
preparing a structure included in a range which is defined by two times as much as a predicted fluctuation value from a target value of the structure of the layer during a process of forming the structure-undetermined layer with the target value used as a center.

15. The method according to claim 13, wherein said preparing determined structures including a structure of the structure-determined layer includes
preparing a structure included in a range which is defined by two times as much as an inspection difference with the structure of the structure-determined layer used as a center.

16. The method according to claim 13, wherein the specified angle includes a plurality of angles.

17. The method according to claim 13, wherein the light includes a plurality of wavelengths.

18. The method according to claim 13, wherein the light intensity is calculated using RCWA (Rigorous coupled-wave analysis) method.

19. A structure inspection method of inspecting a resist pattern which is formed by development of an exposed resist film formed on a substrate, comprising:
predicting an opening shape of a opening where a resist film is dissolved by developer, and predicting a distribution of a mixture ratio of a reaction product of the resist film and the developer in a liquid phase comprising the developer and the reaction product;
preparing an optical constant of the resist film, the reaction product and the developer;
setting structures comprising the substrate and the liquid phase based on the predicted opening shape and mixture ratio;
calculating a light intensity of light which is diffracted from a substrate which has a developer film on a main surface of the substrate when making light enter the substrate at a specified angle;

making light enter at the specified angle a measurement pattern on the substrate which has a developer film on a main surface of the substrate and detecting a light intensity of diffraction light from the substrate;

comparing the detected intensity of the light with the calculated intensity of the light; and calculating at least one of a pattern dimension and a pattern shape of the resist film and the distribution of the ratio in the liquid phase from a best matching result in the comparison.

20. The method according to claim 19, wherein a ratio of the resist film in the mixture ratio in the liquid phase simply decreases to 0 as a position in the liquid phase gets away from an interface where a reaction of the liquid phase and the resist film occurs.

21. The method according to claim 19, wherein the optical constant of the liquid phase is determined based on the mixture ratio.

22. The method according to claim 19, wherein said setting structures, said preparing an optical constant and said calculating the intensity are carried out before the development.

23. The method according to claim 19, wherein said setting structures and said preparing an optical constant are carried out before the development.

24. The method according to claim 19, wherein the light includes a plurality of wavelengths.

25. The method according to claim 19, wherein the light intensity is calculated using RCWA (Rigorous coupled-wave analysis) method.

26. A pattern forming method for evaluating a resist pattern which is formed by development of an exposed resist film formed on a substrate, and completing the development based on the evaluation result, comprising:

predicting an opening shape of a opening where a resist film is dissolved by developer, and predicting a distribution of a mixture ratio of a reaction product of the resist film and the developer in a liquid phase comprising the developer and a reaction product of the resist film;

giving a structure of a construction comprising the substrate and the liquid phase and optical constant based on a result of the prediction;

predicting a light intensity of diffraction light from the construction when making light enter the construction at a specified angle;

making light enter at the specified angle a measurement pattern on the substrate which has a developer film on a main surface of the substrate and detecting an intensity of diffraction light from the substrate;

comparing the detected intensity of the diffraction light with the predicted intensity of the diffraction light;

calculating a pattern dimension of the resist film from a best matching result in the comparison; and completing the development based on the pattern dimension.

27. The method according to claim 26, wherein a ratio of the resist film in the mixture ratio in the liquid phase simply decreases to 0 as a position in the liquid phase gets away from an interface where a reaction of the liquid phase and the resist film occurs.

28. The method according to claim 26, wherein the optical constant of the liquid phase is determined based on the mixture ratio.

29. The method according to claim 26, wherein said giving a structure and optical constant and said predicting the intensity using a calculation are carried out before the development.

30. The method according to claim 26, wherein giving a structure and optical constant is carried out before the development, and predicting the intensity using a calculation is carried out during the development.

31. The method according to claim 26, wherein the light includes a plurality of wavelengths.

32. The method according to claim 26, wherein the light intensity is calculated using RCWA (Rigorous coupled-wave analysis) method.

33. A method of determining a process condition, comprising:

planning an experiment, in which experiment conditions are changed among two or more levels, the experiment conditions including a condition of controlling resist solution, a condition of forming a resist film, an exposure condition of forming a latent image on the resist film, a condition of baking a resist film formed with the latent image, and a condition of developing the resist film to form a resist pattern;

changing exposure amount or defocus amount to form a latent image on the resist film, thereby forming the resist pattern based on the experiment;

carrying out a measurement which includes making light enter at a specified angle a substrate which has a resist pattern thereon, detecting a light intensity of light which is diffracted or reflected from the substrate, and measuring a shape of the resist pattern using the detected light intensity and an optical constant of a material forming the substrate;

calculating a process margin of exposure amount or defocus amount obtained under a level of experiment conditions based on the measured shape of the resist pattern; and predicting a combination of levels of the experiment conditions that realizes a higher process margin than a predetermined value from a relationship between levels of the experiment conditions and the process margin of the exposure amount or defocus amount.

34. The method according to claim 33, wherein at least one of a film thickness, dimension and sectional shape of the resist pattern is measured in the measurement.

35. The method according to claim 33, wherein the measurement is carried out using RCWA (Rigorous coupled-wave analysis) method.

36. A method of determining a process condition, further comprising:

selecting a level of the experiment conditions using the method of determining a process condition according to claim 33;

repeating the method of determining a process condition according to claim 33 while decreasing a number of the experiment conditions to be changed or narrowing a change rage with the selected level of the experiment conditions as a standard; and predicting a combinations of levels of the experiment conditions that realizes a higher process margin than a predetermined value.

37. A method manufacturing a semiconductor device, comprising:

forming a resist pattern on a semiconductor substrate for semiconductor device under a condition determined according to the method of determining a process condition according to claim 33; and processing the substrate using the resist pattern as a mask.

* * * * *